(12) United States Patent
Payyavula et al.

(10) Patent No.: US 12,008,721 B2
(45) Date of Patent: Jun. 11, 2024

(54) MIXED REALITY SYSTEMS AND METHODS FOR INDICATING AN EXTENT OF A FIELD OF VIEW OF AN IMAGING DEVICE

(71) Applicant: Intuitive Surgical Operations, Inc., Sunnyvale, CA (US)

(72) Inventors: Govinda Payyavula, Sunnyvale, CA (US); Cortney Jansen, Sunnyvale, CA (US); Huan Lac Phan, Belmont, CA (US); Simon P. DiMaio, San Carlos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 441 days.

(21) Appl. No.: 17/286,782

(22) PCT Filed: Oct. 24, 2019

(86) PCT No.: PCT/US2019/057962
§ 371 (c)(1),
(2) Date: Apr. 19, 2021

(87) PCT Pub. No.: WO2020/086912
PCT Pub. Date: Apr. 30, 2020

(65) Prior Publication Data
US 2021/0343088 A1    Nov. 4, 2021

Related U.S. Application Data

(60) Provisional application No. 62/751,431, filed on Oct. 26, 2018.

(51) Int. Cl.
*G06T 19/00*    (2011.01)
*A61B 1/00*    (2006.01)
(Continued)

(52) U.S. Cl.
CPC .......... *G06T 19/006* (2013.01); *A61B 1/0005* (2013.01); *A61B 1/05* (2013.01);
(Continued)

(58) Field of Classification Search
CPC ........................... G06T 19/006; A61B 1/0005
See application file for complete search history.

(56) References Cited

U.S. PATENT DOCUMENTS 6,645,196 B1    11/2003    Nixon et al.
7,239,330 B2    7/2007    Sauer et al.
(Continued)

FOREIGN PATENT DOCUMENTS

CN    101193603 A    6/2008
CN    102448680 A    5/2012
(Continued)

OTHER PUBLICATIONS

US 9,980,782 B1, 05/2018, Gibby (withdrawn)
(Continued)

*Primary Examiner* — Oommen Jacob

(57) ABSTRACT

A mixed reality presentation system identifies an operating condition associated with an operation performed on a body while an active imaging device captures imagery of an internal view of the body. The mixed reality presentation system also determines, based on the identified operating condition, that a display device is to toggle a display of a shape overlay that is displayed together with an external view of the body and that is indicative of an extent of a field of view of the active imaging device relative to the body. Based on the determining that the display device is to toggle the display of the shape overlay, the mixed reality presentation system directs the display device to toggle the display of the shape overlay. Corresponding systems and methods are also disclosed.

23 Claims, 15 Drawing Sheets

(51) Int. Cl.
*A61B 1/05* (2006.01)
*A61B 1/06* (2006.01)
*A61B 34/20* (2016.01)
*A61B 34/30* (2016.01)

(52) U.S. Cl.
CPC ............ *A61B 1/0676* (2013.01); *A61B 34/20* (2016.02); *A61B 34/30* (2016.02); *A61B 2034/2057* (2016.02)

(56) References Cited

U.S. PATENT DOCUMENTS

| | | | |
|---|---|---|---|
| 7,774,044 | B2 | 8/2010 | Sauer et al. |
| 8,864,652 | B2 | 10/2014 | Diolaiti et al. |
| 9,326,660 | B2 | 5/2016 | Akimoto et al. |
| 9,645,785 | B1 | 5/2017 | Hannaford et al. |
| 9,681,925 | B2 | 6/2017 | Azar et al. |
| 9,718,190 | B2 | 8/2017 | Larkin et al. |
| 9,767,608 | B2 | 9/2017 | Lee et al. |
| 9,789,608 | B2 * | 10/2017 | Itkowitz ............... A61B 90/361 |
| 9,818,231 | B2 * | 11/2017 | Coffey ................ A61B 34/10 |
| 9,892,564 | B1 | 2/2018 | Cvetko et al. |
| 9,980,780 | B2 | 5/2018 | Lang |
| 10,008,017 | B2 | 6/2018 | Itkowitz et al. |
| 10,010,379 | B1 | 7/2018 | Gibby et al. |
| 10,137,575 | B2 | 11/2018 | Itkowitz et al. |
| 10,235,757 | B2 * | 3/2019 | Hu ....................... A61B 5/4887 |
| 10,579,135 | B2 * | 3/2020 | Urbach ................ G06F 3/0346 |
| 2006/0189842 | A1 | 8/2006 | Hoeg et al. |
| 2006/0281971 | A1 | 12/2006 | Sauer et al. |
| 2007/0021738 | A1 | 1/2007 | Hasser et al. |
| 2007/0236514 | A1 | 10/2007 | Agusanto et al. |
| 2009/0192524 | A1 * | 7/2009 | Itkowitz ................ B25J 9/1692 606/130 |
| 2013/0038707 | A1 | 2/2013 | Cunningham et al. |
| 2015/0366628 | A1 | 12/2015 | Ingmanson |
| 2016/0191887 | A1 | 6/2016 | Casas |
| 2016/0287337 | A1 | 10/2016 | Aram et al. |
| 2017/0056115 | A1 | 3/2017 | Corndorf et al. |
| 2017/0099479 | A1 * | 4/2017 | Browd ................... A61B 34/20 |
| 2017/0128041 | A1 | 5/2017 | Hasser et al. |
| 2017/0128144 | A1 | 5/2017 | Hasser et al. |
| 2017/0128145 | A1 | 5/2017 | Hasser et al. |
| 2017/0135775 | A1 | 5/2017 | Cunningham et al. |
| 2017/0172696 | A1 | 6/2017 | Saget et al. |
| 2017/0209232 | A1 | 7/2017 | Larkin et al. |
| 2017/0210012 | A1 | 7/2017 | Larkin et al. |
| 2017/0305016 | A1 | 10/2017 | Larkin et al. |
| 2017/0344674 | A1 * | 11/2017 | McCloskey ........... G06T 19/006 |
| 2018/0032130 | A1 | 2/2018 | Meglan |
| 2018/0116732 | A1 | 5/2018 | Lin et al. |
| 2018/0140362 | A1 | 5/2018 | Caliet al. |
| 2019/0088162 | A1 | 3/2019 | Meglan |
| 2019/0156402 | A1 * | 5/2019 | Greenberger ...... G06Q 30/0643 |
| 2019/0183576 | A1 | 6/2019 | Fahim et al. |
| 2019/0231453 | A1 | 8/2019 | Carnes et al. |
| 2020/0054412 | A1 | 2/2020 | Fuerst et al. |
| 2021/0228282 | A1 | 7/2021 | Dimaio et al. |
| 2021/0338366 | A1 | 11/2021 | Payyavula et al. |
| 2021/0343088 | A1 * | 11/2021 | Payyavula ............. A61B 34/20 |

FOREIGN PATENT DOCUMENTS

| | | |
|---|---|---|
| EP | 1294285 A1 | 3/2003 |
| EP | 2289452 A2 | 3/2011 |
| EP | 2289453 A2 | 3/2011 |
| EP | 2289454 A2 | 3/2011 |
| EP | 2046538 B1 | 12/2011 |
| EP | 1887961 B1 | 1/2012 |
| EP | 2414137 A2 | 2/2012 |
| EP | 2471484 A2 | 7/2012 |
| JP | 2009542362 A | 12/2009 |
| JP | 2012050887 A | 3/2012 |
| JP | 2012050888 A | 3/2012 |
| JP | 2012055717 A | 3/2012 |
| JP | 4999012 B2 | 8/2012 |
| JP | 2012521855 A | 9/2012 |
| JP | 2012213655 A | 11/2012 |
| JP | 2013188574 A | 9/2013 |
| JP | 2013252452 A | 12/2013 |
| JP | 2014138901 A | 7/2014 |
| JP | 2016052521 A | 4/2016 |
| JP | 2016064155 A | 4/2016 |
| JP | 2016101506 | 6/2016 |
| KR | 20080027224 A | 3/2008 |
| KR | 20090034813 A | 4/2009 |
| KR | 20120004479 A | 1/2012 |
| WO | WO-0197694 A1 | 12/2001 |
| WO | WO-2007030173 A1 | 3/2007 |
| WO | WO-2008002830 A2 | 1/2008 |
| WO | WO-2010117685 A2 | 10/2010 |
| WO | WO-2016162789 A3 | 11/2016 |
| WO | WO-2016207628 A1 | 12/2016 |
| WO | WO-2017151752 A1 | 9/2017 |
| WO | WO-2017151999 A1 | 9/2017 |
| WO | WO-2018005842 A1 | 1/2018 |
| WO | WO-2018032083 A1 | 2/2018 |
| WO | WO-2018052966 A1 | 3/2018 |
| WO | WO-2018118411 A1 | 6/2018 |

OTHER PUBLICATIONS

Extended European Search Report for Application No. EP22166192. 9, dated Jun. 28, 2022, 9 pages.

Carbone M. et al., "Proof of Concept: Wearable Augmented Reality Video SeeThrough Display for Neuro-Endoscopy", International Conference on Financial Cryptography and Data Security, Jul. 14, 2018, pp. 95-104.

Hedayati H., et al., "Improving Collocated Robot Teleoperation with Augmented Reality, " Human-Robot Interaction, ACM, Feb. 26, 2018, pp. 78-86.

International Search Report and Written Opinion for Application No. PCT/US2019/057962, dated Jan. 24, 2020, 9 pages.

International Search Report and Written Opinion for Application No. PCT/US2019/057961, dated Feb. 7, 2020, 10 pages.

Qian L., et al., "ARssist: augmented reality on a head-mounted display for the first assistant in robotic surgery," Healthcare Technology Letters, Sep. 2018, vol. 5 (5), pp. 194-200.

Trevisan D.G., et al., "Augmented Vision for Medical Applications," Proceedings ACM SAC, Mar. 16, 2008, pp. 415-1419.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2019/057961, dated May 6, 2021, 08 pages.

International Preliminary Report on Patentability for Application No. PCT/US2019/057962, dated May 6, 2021, 07 pages.

* cited by examiner

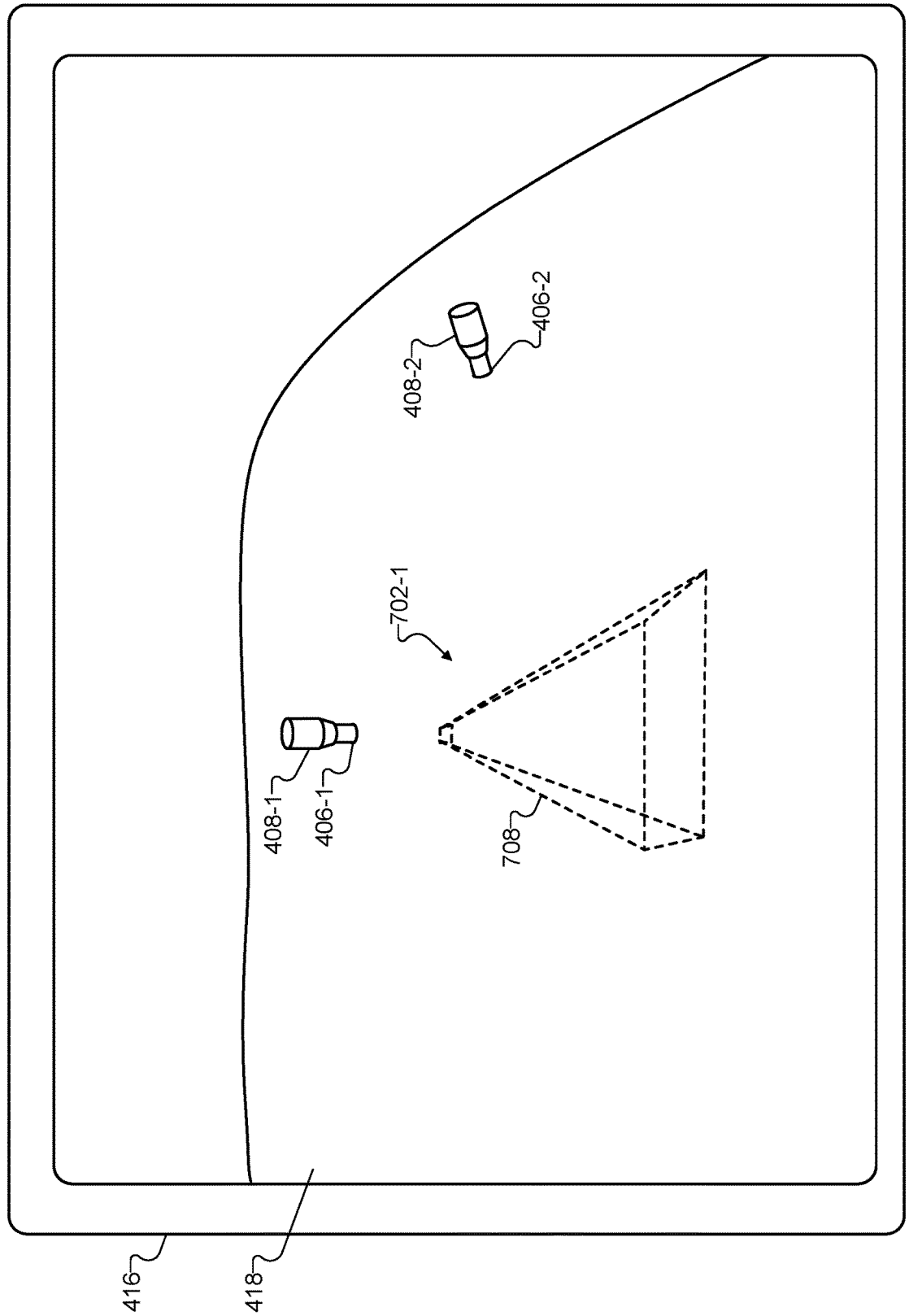

MIXED REALITY SYSTEMS AND METHODS FOR INDICATING AN EXTENT OF A FIELD OF VIEW OF AN IMAGING DEVICE

RELATED APPLICATIONS

The present application is a U.S. National Stage Application under 35 U.S.C. § 371 of International Application No. PCT/US2019/057962, filed on Oct. 24, 2019, and entitled "MIXED REALITY SYSTEMS AND METHODS FOR INDICATING AN EXTENT OF A FIELD OF VIEW OF AN IMAGING DEVICE," which claims priority to U.S. Provisional Patent Application No. 62/751,431, filed on Oct. 26, 2018, and entitled "MIXED REALITY SYSTEMS AND METHODS FOR INDICATING AN EXTENT OF A FIELD OF VIEW OF AN IMAGING DEVICE," the contents of which are hereby incorporated by reference in their entirety.

BACKGROUND INFORMATION

During an operation being performed within a partially or wholly confined space, an imaging device may capture and provide an internal view of the confined space. For example, a minimally invasive medical procedure such as a diagnostic or surgical procedure using a computer-assisted medical system may be performed to operate on tissue inside a body of a patient, and an imaging device such as an endoscope may be used during the operation to capture and provide an internal view of the body.

In some examples, it may be desirable for a person involved in performing the operation (e.g., an assistant who is assisting with the procedure) to perform actions associated with the confined space and/or parts of the confined space depicted by the internal view provided by the imaging device. For instance, if the operation is a medical procedure such as a minimally invasive surgical procedure, it may be desirable during the operation for an assistant to insert instruments, supplies, or the like into the confined space in such a way that the inserted objects can be readily seen and easily used by a clinician looking at the internal view provided by the imaging device.

The imaging device capturing the internal view of the partially or wholly confined space may be at least partially hidden from view from the perspective of the person attempting to perform the actions associated with the confined space. As such, in order to effectively perform the desired actions, the person typically has to mentally visualize the location and orientation of the imaging device and its field of view.

SUMMARY

Mixed reality systems and methods for indicating an extent of a field of view of an imaging device are described herein. For instance, one embodiment is implemented as a system comprising a memory storing instructions and a processor communicatively coupled to the memory and configured to execute the instructions. For example, the instructions may direct the processor to identify an operating condition associated with an operation performed on a body while an active imaging device captures imagery of an internal view of the body. The instructions may also direct the processor to determine, based on the identified operating condition, that a display device is to toggle a display of a shape overlay that is displayed together with an external view of the body, the shape overlay indicative of an extent of a field of view of the active imaging device relative to the body. Based on the determining that the display device is to toggle the display of the shape overlay, the instructions may further cause the processor to direct the display device to toggle the display of the shape overlay.

Another exemplary embodiment is implemented as a method performed by a mixed reality presentation system. For example, the method includes identifying an operating condition associated with an operation performed on a body while an active imaging device captures imagery of an internal view of the body. The method further includes determining, based on the identified operating condition, that a display device is to toggle a display of a shape overlay that is displayed together with an external view of the body, the shape overlay indicative of an extent of a field of view of the active imaging device relative to the body. Additionally, the method includes directing, based on the determining that the display device is to toggle the display of the shape overlay, the display device to toggle the display of the shape overlay.

Another exemplary embodiment is implemented by a non-transitory, computer-readable medium storing instructions that, when executed, direct a processor of a computing device to perform operations described herein. For example, the instructions may direct the processor to identify an operating condition associated with an operation performed on a body while an active imaging device captures imagery of an internal view of the body. The instructions may further direct the processor to determine, based on the identified operating condition, that a display device is to toggle a display of a shape overlay that is displayed together with an external view of the body, the shape overlay indicative of an extent of a field of view of the active imaging device relative to the body. based on the determining that the display device is to toggle the display of the shape overlay, the instructions may cause the processor to direct the display device to toggle the display of the shape overlay.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 11A-11D illustrate an exemplary display device displaying different exemplary shape overlays to facilitate a process of moving or swapping out an active imaging device according to principles described herein.

DETAILED DESCRIPTION

Figure 1:
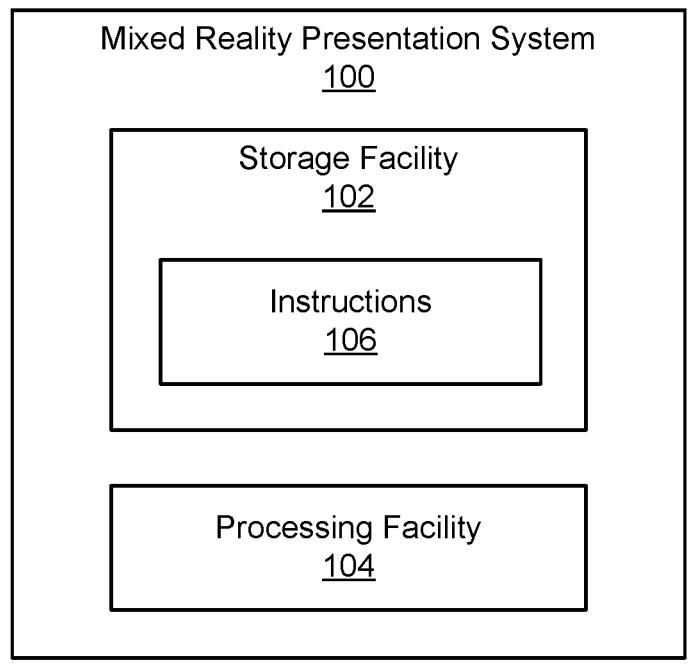
FIG. 1 illustrates an exemplary mixed reality presentation system for indicating an extent of a field of view of an imaging device according to principles described herein.

Mixed reality presentation systems and methods for indicating an extent of a field of view of an imaging device are described herein. For example, in order to facilitate a performance of an operation within a partially or wholly confined space, systems and methods disclosed herein use mixed reality technology to display a shape overlay together with a real external view. Examples of an operation within a partially or wholly confined space include medical procedures such as minimally invasive surgical or non-surgical medical procedures performed with artificial or natural orifices. Examples of shape overlays include graphics depicting, possibly among other virtual objects, virtual geometric shapes such as three-dimensional ("3D") frusta or other shapes. As used herein, mixed reality technology may refer to any technology providing an immersive reality that combines real and virtual elements (e.g., augmented reality technology, augmented virtuality technology, etc.). Thus, in this way, a user of the mixed reality systems and methods described herein may quickly and easily understand an extent (e.g., a shape, a location, an orientation, etc.) of a field of view of an imaging device capturing imagery of an operational area that is not viewable from the user's perspective. As such, the user may avoid having to mentally visualize part or the entirety of the field of view when performing actions for which a static or dynamic understanding of the field of view extent may be useful.

Aspects of the mixed reality presentation systems and methods described herein primarily relate to implementations employing a computer-aided medical system such as a minimally invasive surgical system. As will be described in more detail below, however, it will be understood that inventive aspects disclosed herein may be embodied and implemented in various ways, including by employing robotic and non-robotic embodiments and implementations. Implementations relating to surgical or other medical systems are merely exemplary and are not to be considered as limiting the scope of the inventive aspects disclosed herein. For example, any reference to surgical instruments, surgical techniques, and/or other such details relating to a surgical context will be understood to be non-limiting as the instruments, systems, and methods described herein may be used for medical treatment or diagnosis, cosmetic improvements, imaging of human or animal anatomy, gathering data from human or animal anatomy, setting up or taking down systems, training medical or non-medical personnel, and so forth (any of which may or may not also involve surgical aspects). In other examples, the instruments, systems, and methods described herein may also be used for procedures performed on, or with, animals, human cadavers, animal cadavers, portions of human or animal anatomy, tissue removed from human or animal anatomies (which may or may not be re-implanted within the human or animal anatomy), non-tissue work pieces, training models, etc. In yet other examples, the instruments, systems, and methods described herein may be applied for non-medical purposes including for industrial systems, general robotics, teleoperational systems, and/or sensing or manipulating non-tissue work pieces.

As one exemplary implementation, a mixed reality presentation system may include or be implemented by a memory storing instructions and a processor communicatively coupled to the memory and configured to execute the instructions to perform functionality associated with indicating the extent of the field of view of the imaging device.

For example, the mixed reality presentation system may identify an operating condition associated with an operation performed on a body (e.g., a body of a live patient or another suitable body that may be living or non-living, biological or non-biological, natural or artificial, etc.). The operation may be performed within the body or at another partially or entirely confined space associated with the body. As such, an active imaging device may capture imagery of an internal view of the body during the operation. For example, the active imaging device may be an imaging device that is being used or prepared for use to actively capture imagery of the internal view of the body during an ongoing or imminent operation.

As will be described in more detail below, the operating condition identified by the mixed reality presentation system may be any suitable operating condition as may serve a particular implementation. For example, the operating condition may relate to a state of an operating instrument associated with the operation (e.g., the active imaging device, another instrument employed to perform the operation, etc.), a spatial pose (e.g., position and orientation) of the operating instrument, an action performed by the operating instrument, or another aspect associated with operating instruments or systems enabling or facilitating the operation. Additionally or alternatively, the operating condition may include a state or condition of the body upon which the operation is performed, of one or more people performing the operation, or of the operation itself. Examples of operating conditions that may be identified by mixed reality presentation systems disclosed herein will be described in more detail below.

Based on the identified operating condition, the mixed reality presentation system may determine that a display device (e.g., a mixed reality headset, a display monitor, etc.) is to toggle a display of a shape overlay that is displayed together with an external view of the body. The shape overlay may include one or more virtual objects (including, as mentioned above, a geometrical shape, as well as other virtual objects in certain examples) that graphically indicate an extent of a field of view of the active imaging device relative to the body. The external view may be a photographic representation from a vantage point of a user (e.g., a representation captured using a camera integrated into a display device viewed by the user) or a direct view that the user has from the vantage point (e.g., through a partially transparent screen of the display device). Various examples will be described below of operating conditions that may cause the mixed reality presentation system to determine that the display of the shape overlay is to be toggled (i.e., switched to an on or off state that is opposite from the current state of the display) for various reasons and/or in various contexts.

Based on the determining that the display device is to toggle the display of the shape overlay, the mixed reality presentation system may direct the display device to toggle the display of the shape overlay. For example, if the shape overlay is not currently being displayed by the display device, the mixed reality presentation system may direct the display device to toggle the display by turning on (i.e., beginning to present) the display of the shape overlay. As another example, instead of or in addition to the foregoing, if the shape overlay is currently being displayed by the display device, the mixed reality presentation system may direct the display device to toggle the display by turning off (i.e., ceasing to present) the display of the shape overlay.

When displayed, the shape overlay may be presented together with the external view. For instance, the shape overlay may be presented as a virtual object integrated with (e.g., graphically overlaid onto so as to appear to be integrated with) real objects visible in the external view to present a mixed reality presentation to the user. Accordingly, by viewing the display of the shape overlay, the user may instantly and conveniently see and understand the extent of the field of view of the active imaging device even though at least part of the active imaging device (e.g., a distal end of the imaging device capturing the internal view) may not be visible to the user within the external view.

In these examples, the shape overlay may graphically indicate the extent of the field of view of the active imaging device relative to the body in any suitable manner. For example, by being integrated with the external view of the body, the display of the shape overlay may indicate the extent of the field of view by graphically depicting attributes of the field of view (e.g., a shape of the field of view, a size or width of the field of view, etc.), as well as by depicting one or more parameters of a spatial pose of the field of view (e.g., one or more spatial position parameters, one or more spatial orientation parameters, a combination of spatial and orientation parameters, etc.) as the active imaging device captures imagery of the internal view. Accordingly, as used herein, an extent of the field of view may refer to both shape and size-type attributes of the field of view as well as to dynamic pose-type attributes (e.g., location, orientation, etc.) of the field of view.

Various benefits may be provided by the mixed reality presentation systems and methods described herein. For example, as mentioned above, challenging operations performed in partially or wholly confined spaces (e.g., minimally invasive medical procedures performed within bodies of patients, etc.) may be facilitated and made more effective and efficient when persons performing the operations can easily and dynamically see and understand an extent of a field of view of the active imaging device.

In certain implementations, for instance, an assistant who is helping to perform a medical procedure may be tasked with inserting an instrument or other object (e.g., supplies such as patching materials, suturing materials, etc.) into an operational area within a body. The assistant may perform this task easily, timely, and effectively if the assistant can see the extent of a field of view of an active imaging device providing an internal view to a surgeon. For example, as described above, a shape overlay that graphically illustrates the extent of the field of view by being integrated with, overlaid onto, or otherwise presented together with, an external view of the body (e.g., by way of a mixed reality headset device, a mixed-reality-enabled display monitor device, etc.). In some cases, the assistant may perform the task more easily, timely, and effectively if the shape overlay is presented to augment the assistant's understanding of the internal geometry of the operational area than if the assistant has to mentally visualize the internal geometry without the aid of the mixed reality presentation.

Moreover, the mixed reality systems and methods described herein are beneficial in certain implementations not only for indicating an accurate, real-time extent of the field of view, but for doing so automatically when (and, in some examples, only when) such an indication is determined to be appropriate based on real-time operating conditions. For example, when operating conditions are such that the mixed reality presentation system determines that it is likely to be helpful or desirable to a user for the shape overlay to be displayed, the mixed reality presentation system may automatically direct the display of the shape overlay to toggle on. Similarly, when operating conditions are such that the mixed reality presentation system determines that the display of the shape overlay is likely to be unnecessary or undesirable (e.g., distracting), the mixed reality presentation system may automatically direct the display of the shape overlay to toggle off.

Various embodiments will now be described in more detail with reference to the figures. The systems and methods described herein may provide one or more of the benefits mentioned above as well as various additional and/or alternative benefits that will be made apparent by the description below.

FIG. 1 illustrates an exemplary mixed reality presentation system 100 ("system 100"). As shown, system 100 may include, without limitation, a storage facility 102 and a processing facility 104 selectively and communicatively coupled to one another. Facilities 102 and 104 may each include or be implemented by hardware and/or software components (e.g., processors, memories, communication interfaces, instructions stored in memory for execution by the processors, etc.). In some examples, facilities 102 and 104 may be distributed between multiple devices and/or multiple locations as may serve a particular implementation.

Storage facility 102 may maintain (e.g., store) executable data used by processing facility 104 to perform any of the functionality described herein. For example, storage facility 102 may store instructions 106 that may be executed by processing facility 104 to perform any of the functionality described herein. Instructions 106 may be implemented by any suitable application, software, code, and/or other executable data instance. Storage facility 102 may also maintain any data received, generated, managed, used, and/or transmitted by processing facility 104.

Processing facility 104 may be configured to perform (e.g., execute instructions 106 stored in storage facility 102 to perform) various processing functions associated with indicating an extent of a field of view of an imaging device. For example, processing facility 104 may identify an operating condition associated with an operation performed on a body while an active imaging device captures imagery of an internal view of the body. Based on the identified operating condition, processing facility 104 may determine that a display device is to toggle a display of a shape overlay that is displayed together with an external view of the body. The shape overlay may be indicative of an extent of a field of view of the active imaging device relative to the body.

Based on the determining that the display device is to toggle the display of the shape overlay, processing facility 104 may direct the display device to toggle the display of the shape overlay. For instance, in some examples, processing facility 104 may be configured to determine (e.g., in response to the identifying of the operating condition) a current display status of the shape overlay and direct the display device to toggle the display of the shape overlay based on the current display status. For example, processing facility 104 may direct the display device to toggle by beginning to display the shape overlay together with the external view if the current display status indicates that the shape overlay is not displayed when the operating condition is identified. As another example, instead of or in addition to the foregoing, if the current display status indicates that the shape overlay is displayed when the operating condition is identified, processing facility 104 may direct the display device to toggle by ceasing to display the shape overlay together with the external view.

In some implementations, system 100 (e.g., processing facility 104) may be configured to direct the display device to toggle and/or update the display of the shape overlay in real time. As used herein, a function may be said to be performed in real time when the function relates to or is based on dynamic, time-sensitive information and the function is performed while the time-sensitive information remains accurate or otherwise relevant. Due to processing times, communication latency, and other inherent delays in physical systems, certain functions may be considered to be performed in real time when performed immediately and without undue delay, even if performed after small delay (e.g., a delay up to a few seconds or the like). As one example of real-time functionality, one or more operating conditions may dynamically change as an operation is ongoing and as the active imaging device captures the imagery of the internal view of the body. Thus, the determination that the display device is to toggle the display of the shape overlay may be performed in real time by determining, immediately after the operating condition is detected to change, that the toggling is to be performed. As another example, the display device may be directed to display the shape overlay in real time by immediately and continuously updating the shape overlay based on the dynamic extent of the field of view as the pose of the active imaging device dynamically changes in relation to the external view of the body.

Along with determining that the display device is to toggle the display of the shape overlay and directing the display device to perform this toggling operation, system 100 (e.g., processor facility 104) may further automatically determine other aspects of how and/or whether the shape overlay is to be displayed, and may direct the display device accordingly. For example, based on one or more operating conditions, system information, user configuration information, and/or any other suitable information, system 100 may direct the display device to display more than one shape overlay concurrently, display a shape overlay in a particular manner, and/or perform any of the shape overlay display operations described herein or as may serve a particular implementation.

System 100 may be used in various contexts with various different types of technologies as may serve a particular implementation. For example, system 100 may be effectively used in a medical context such as a computer-assisted medical procedure in which an operation is performed inside of any suitable type of body as may serve a particular implementation. For instance, the medical procedure may be performed within a body of a live human patient, within a body of a cadaver being used for training purposes, within a body of a non-human subject (e.g., an animal or the like), or any other suitable biological body. In some examples, the body within which the operation is performed may be only an anatomical portion of one of these other types of bodies. For example, the body within which the operation is performed may be a disembodied organ or other body part taken from a full biological body (e.g., to be used for training purposes), or may be an artificial training fixture (e.g., an artificial organ or other body part) used for training, experimental, and/or other such purposes.

In other implementations, system 100 may be used in medical contexts where imaging devices or tools are not controlled by computer-assistance (e.g., laparoscopic procedures that do not involve robotic or computer-assisted control of system components), or that are not surgical in nature (e.g., diagnostic or exploratory imaging without surgical elements), or that are not for treatment or diagnosis (e.g., training or other procedures that do not involve treatment). Additionally, in certain implementations, system 100 may be used in non-medical contexts. For instance, system 100 may be useful for performing inspection or repair operations within bodies of complex electrical or mechanical systems such engines and other complex systems. As another example, system 100 may be used in law enforcement or surveillance contexts (e.g., to inspect and disable dangerous explosive devices, to conduct surveillance in tight spaces, etc.), and/or in any other contexts or with any other technologies as may serve a particular implementation.

One exemplary context in which system 100 may be used will now be described. Specifically, system 100 may operate as part of or in conjunction with a computer-assisted medical system. The exemplary computer-assisted medical system described below is illustrative and not limiting. It will be understood that mixed reality systems and methods described herein may operate as part of or in conjunction with the computer-assisted medical system described herein, with other suitable computer-assisted medical systems that may or may not be surgical systems, and/or with other suitable medical and/or non-medical systems as may serve a particular implementation.

Figure 2:
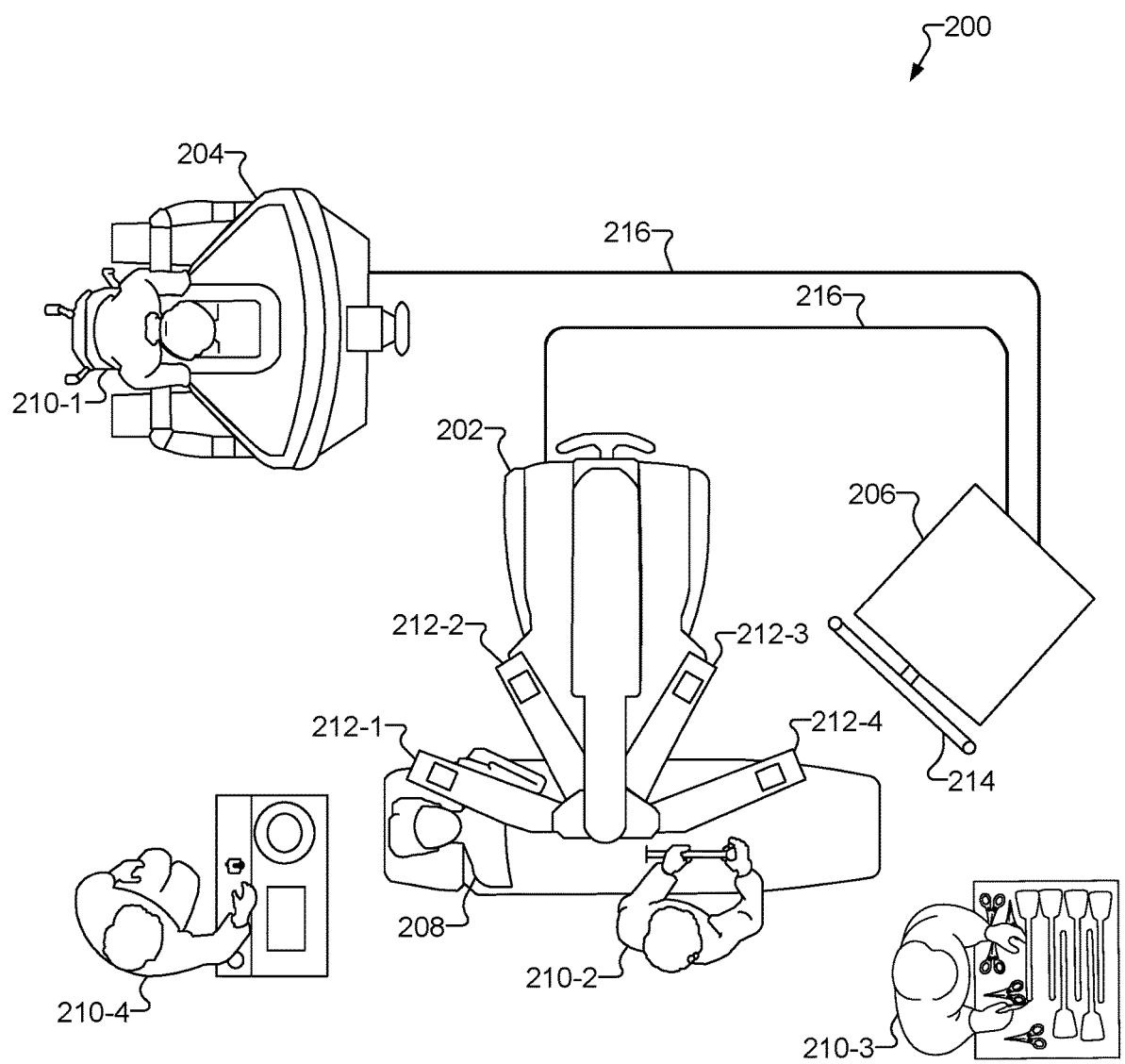
FIG. 2 illustrates an exemplary computer-assisted medical system according to principles described herein.

FIG. 2 illustrates an exemplary computer-assisted medical system 200 ("medical system 200") that may be used to perform surgical and/or non-surgical medical procedures. As shown, medical system 200 may include a manipulating system 202, a user control system 204, and an auxiliary system 206 communicatively coupled one to another. Medical system 200 may be utilized by a medical team to perform a computer-assisted medical procedure or other such operation on a body of a patient 208 or any other body as may serve a particular implementation. As shown, the medical team may include a first clinician 210-1 (such as a surgeon for a surgical procedure), an assistant 210-2, a nurse 210-3, and a second clinician 210-4 (such as an anesthesiologist for a surgical procedure), all of whom may be collectively referred to as "team members 210," and each of whom may control, interact with, or otherwise be a user of medical system 200. Additional, fewer, or alternative team members may be present during a medical procedure as may serve a particular implementation. For example, for some medical procedures, clinician 210-1 may not be a medical doctor. Further, team composition for non-medical procedures generally differ, and include other combinations of members serving non-medical roles.

While FIG. 2 illustrates an ongoing minimally invasive medical procedure such as a minimally invasive surgical procedure, it will be understood that medical system 200 may similarly be used to perform open medical procedures or other types of operations that may similarly benefit from the accuracy and convenience of medical system 200. For example, operations such as exploratory imaging operations, mock medical procedures used for training purposes, and/or other operations may also be performed using medical system 200. Additionally, it will be understood that any medical procedure or other operation for which medical system 200 is employed may not only include an operative phase, but may also include preoperative, postoperative, and/or other such operative phases.

As shown in FIG. 2, manipulating system 202 may include a plurality of manipulator arms 212 (e.g., manipulator arms 212-1 through 212-4) to which a plurality of instruments (e.g., surgical instruments, other medical instruments, or other instruments, etc.) may be coupled. Each instrument may be implemented by any suitable surgical tool (e.g., a tool having tissue-interaction functions), medical tool, imaging device (e.g., an endoscope), sensing instrument (e.g., a force-sensing instrument), diagnostic instrument, or the like that may be used for a computer-assisted medical procedure such as a surgical procedure on patient 208 (e.g., by being at least partially inserted into patient 208 and manipulated to perform a computer-assisted medical procedure on patient 208). While manipulating system 202 is depicted and described herein as including four manipulator arms 212, it will be recognized that manipulating system 202 may include only a single manipulator arm 212 or any other number of manipulator arms as may serve a particular implementation. Additionally, it will be understood that, in some exemplary systems, certain instruments may not be coupled to or controlled by manipulator arms, but rather may be handheld and controlled manually (e.g., by a surgeon, other clinician, or other medical personnel). For instance, certain handheld devices of this type may be used in conjunction with or as an alternative to computer-assisted instrumentation that is coupled to manipulator arms 212 shown in FIG. 2 and is described in various examples herein.

Manipulator arms 212 and/or instruments attached to manipulator arms 212 may include one or more displacement transducers, orientational sensors, and/or positional sensors used to generate raw (i.e., uncorrected) kinematics information. One or more components of medical system 200 may be configured to use the kinematics information to track (e.g., determine positions of) and/or control the instruments.

Instruments attached to manipulator arms 212 may each be positioned at an operational area associated with patient 208. As used herein, an "operational area" associated with a body (e.g., a body of patient 208 or another type of body being operated upon such as described above) may, in certain examples, be entirely disposed within the body and may include an area within the body near where an operation (e.g., a medical procedure) is planned to be performed, is being performed, or has been performed. For example, for a minimally invasive medical procedure being performed on tissue internal to a patient, the operational area may include the tissue, anatomy underlying the tissue, as well as space around the tissue where, for example, instruments being used to perform the operation are located. In other examples, an operational area may be at least partially disposed external to the body. For instance, medical system 200 may be used to perform an open medical procedure such that part of the operational area (e.g., tissue being operated on) is internal to the body while another part of the operational area (e.g., a space around the tissue where one or more instruments may be disposed) is external to the body. A instrument may be referred to as being located at or within an operational area when at least a portion of the instrument (e.g., a distal end of the instrument) is located within the operational area.

User control system 204 may be configured to facilitate control by clinician 210-1 of manipulator arms 212 and instruments attached to manipulator arms 212. For example, clinician 210-1 may interact with user control system 204 to remotely move or manipulate manipulator arms 212 and the instruments. To this end, user control system 204 may provide clinician 210-1 with imagery (e.g., high-definition 3D imagery) of an operational area associated with patient 208 as captured by an imaging device. In some examples, this captured imagery may be referred to as imagery of an internal view of the body of patient 208. In certain examples, user control system 204 may include a stereo viewer having two displays where stereoscopic images of the internal view of the body of patient 208 generated by a stereoscopic imaging device may be viewed by clinician 210-1. Clinician 210-1 may utilize the imagery to perform one or more procedures with one or more instruments attached to manipulator arms 212.

To facilitate control of instruments, user control system 204 may include a set of master controls. These master controls may be manipulated by clinician 210-1 to control movement of instruments (e.g., by utilizing robotic and/or teleoperation technology). The master controls may be configured to detect a wide variety of hand, wrist, and finger movements by clinician 210-1. In this manner, clinician 210-1 may intuitively perform a procedure using one or more instruments.

Auxiliary system 206 may include one or more computing devices configured to perform primary processing operations of medical system 200. In such configurations, the one or more computing devices included in auxiliary system 206 may control and/or coordinate operations performed by various other components of medical system 200 such as manipulating system 202 and/or user control system 204. For example, a computing device included in user control system 204 may transmit instructions to manipulating system 202 by way of the one or more computing devices included in auxiliary system 206. As another example, auxiliary system 206 may receive and process image data representative of imagery captured by an imaging device attached to one of manipulator arms 212.

In some examples, auxiliary system 206 may be configured to present visual content to team members 210 who may not have other access to the images provided to clinician 210-1 at user control system 204. To this end, auxiliary system 206 may include a display monitor 214 configured to display one or more user interfaces, one or more images (e.g., 2D images) of the operational area, information associated with patient 208 and/or the medical procedure, and/or any other content as may serve a particular implementation. In some examples, display monitor 214 may display images of an internal view of the operational area together with additional content (e.g., graphical content, contextual information, etc.) concurrently displayed with the images. Display monitor 214 may be implemented by a touchscreen display with which team members 210 may interact (e.g., by way of touch gestures) to provide user input to medical system 200, or may be implemented by any other type of display screen as may serve a particular implementation.

As will be described in more detail below, system 100 may be implemented within or may operate in conjunction with medical system 200. For instance, in certain implementations, system 100 may be implemented by auxiliary system 206 (e.g., using a display device such as display monitor 214) or by another device such as a device worn by a team member 210 (e.g., assistant 210-2). As such, and as will be described and illustrated in more detail below, auxiliary system 206 may be configured to also display, along with displaying images of the internal view, images of an external view of the body (e.g., the body of patient 208) together with which a shape overlay indicative of the extent of a field of view of an imaging device may be displayed in accordance with principles described herein.

Manipulating system 202, user control system 204, and auxiliary system 206 may be communicatively coupled one to another in any suitable manner. For example, as shown in FIG. 2, manipulating system 202, user control system 204, and auxiliary system 206 may be communicatively coupled by way of control lines 216, which may represent any wired or wireless communication link as may serve a particular implementation. To this end, manipulating system 202, user control system 204, and auxiliary system 206 may each include one or more wired or wireless communication interfaces, such as one or more local area network interfaces, Wi-Fi network interfaces, cellular interfaces, etc.

Figure 3:
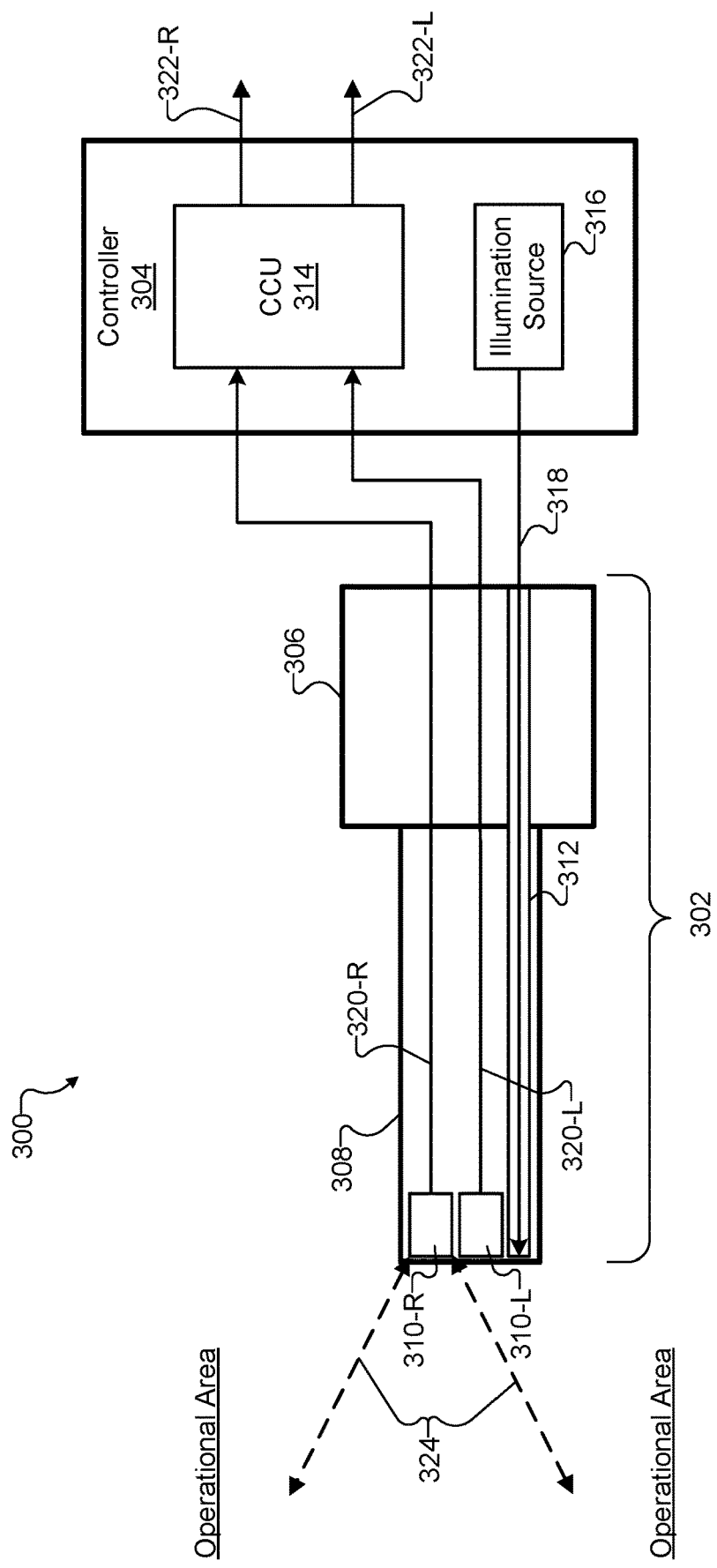
FIG. 3 illustrates an exemplary imaging device located at an operational area according to principles described herein.

FIG. 3 illustrates an exemplary imaging system 300 that may be used in accordance with the systems and methods described herein to capture images of an internal view of a body (e.g., images of an operational area within the body). As shown, imaging system 300 includes an imaging device 302 and a controller 304. Imaging system 300 may include additional or alternative components as may serve a particular implementation. For example, imaging system 300 may include various optical and/or electrical signal transmission components (e.g., wires, lenses, optical fibers, choke circuits, waveguides, etc.), a cable that houses electrical wires and/or optical fibers and that is configured to interconnect imaging device 302 and controller 304, or the like.

Imaging device 302 may be implemented by an endoscope or similar such imaging tool (e.g., a laparoscope, etc.) configured to capture imagery of a scene such as an internal view of any of the bodies described herein. In the example of FIG. 3, imaging device 302 is stereoscopic. In other examples, however, imaging device 302 may be monoscopic (e.g., by including one image sensor instead of two image sensors). Additionally, while imaging devices such as endoscopes, laparoscopes, and so forth may detect light in confined operational areas in the manner described herein in relation to FIG. 3, it will be understood that other imaging technologies (e.g., ultrasound imaging, imaging outside of the visible light range, etc.) and other types of imaging devices or combinations of devices may be used to capture an internal view of a body in other examples.

For instance, ultrasound imaging or other such technologies may be employed in certain examples in which an imaging device includes an ultrasound probe that is inserted into an operational area and may be manipulated using instruments attached to manipulator arms, rather than being controlled by itself being directly attached to a manipulator arm. As another example, hyperspectral imaging technologies and tools may be used to capture images in other regions of the electromagnetic spectrum other than the visible light spectrum. This may facilitate, for example, imaging of features (e.g., blood vessels, etc.) that may be underneath an outer surface that reflects visible light. Similarly, performing infrared, ultraviolet, or other hyperspectral imaging may allow for imaging techniques in which fluorescent imaging agents are injected into tissue to highlight different features at different times due to known metabolization and/or decomposition patterns of the imaging agents. Such imaging technologies may be implemented by different modalities supported by a single imaging system (e.g., imaging system 300) or by different imaging systems (e.g., an imaging system that may be swapped in for imaging system 300 if desired by the medical team performing the operation).

As shown, imaging device 302 includes a camera head 306, a shaft 308 coupled to and extending away from camera head 306, image sensors 310 (i.e., a right-side image sensor 310-R and a left-side image sensor 310-L) at a distal end of shaft 308, and an illumination channel 312. Each of these elements will now be described in more detail.

Imaging device 302 may be manually handled and controlled (e.g., by a surgeon, other clinician, or assistant performing or supporting a medical procedure on a patient). Alternatively, camera head 306 may be coupled to a manipulator arm of a computer-assisted medical system (e.g., one of manipulator arms 212 of medical system 200) and controlled using robotic and/or teleoperation technology.

The distal end of shaft 308 may be positioned at an operational area that is to be imaged by imaging device 302 (e.g., an operational area included within a patient's body or another suitable body as described herein). In this configuration, imaging device 302 may be used to capture images of anatomy and/or other objects within the operational area. In various implementations, shaft 308 is rigid (as shown in FIG. 3). Alternatively, shaft 308 may be jointed (e.g., including an articulation mechanism to allow for wrist-like movement and control) and/or may be flexible. Additionally, while the distal end of shaft 308 is shown in this example to terminate at an orthogonal angle in relation to the axis of shaft 308 such that imaging device 302 captures imagery of objects around the axis of shaft 308 (i.e., objects that are straight ahead), in other examples, the distal end of shaft 308 may be tapered at an angle (e.g., a 30° angle, a 45° angle, etc.) that is non-orthogonal to the axis of shaft 308. In this way, imaging device 302 may capture imagery of objects that are offset from the axis of shaft 308, thereby allowing for more flexibility in where a field of view of imaging device 302 may be directed.

Image sensors 310 may each be implemented by any suitable image sensor, such as a charge coupled device ("CCD") image sensor, a complementary metal-oxide semiconductor ("CMOS") image sensor, or the like. In some examples, as shown in FIG. 3, image sensors 310 are positioned at the distal end of shaft 308. Alternatively, image sensors 310 may be positioned closer to a proximal end of shaft 308, inside camera head 306, or outside imaging device 302 (e.g., inside controller 304). In these alternative configurations, optics (e.g., lenses, optical fibers, etc.) included in shaft 308 and/or camera head 306 may convey light from a scene to image sensors 310.

Image sensors 310 are configured to detect (e.g., capture, collect, sense, or otherwise acquire) light. For example, image sensor 310-R is configured to detect the light from a right-side perspective, and image sensor 310-L is configured to detect the light from a left-side perspective. The light detected by image sensors 310 may include, for example, visible light reflecting off objects located within the operational area, hyperspectral (i.e., non-visible) light reflecting off the objects, fluorescence illumination generated by a fluorescence imaging agent in the operational area, or any other light having any frequency as may serve a particular implementation. As described in more detail below, image sensors 310 may convert the detected light into data representative of one or more images.

Illumination channel 312 may be implemented by one or more optical components (e.g., optical fibers, light guides, lenses, etc.). As will be described below, illumination may be provided by way of illumination channel 312 to illuminate the operational area and the objects included therein.

Controller 304 may be implemented by any suitable combination of hardware and software configured to control and/or interface with imaging device 302. For example, controller 304 may be at least partially implemented by a computing device included in auxiliary system 206.

Controller 304 includes a camera control unit ("CCU") 314 and an illumination source 316. Controller 304 may include additional or alternative components as may serve a particular implementation. For example, controller 304 may include circuitry configured to provide power to components included in imaging device 302. In some examples, CCU 314 and/or illumination source 316 are alternatively included in imaging device 302 (e.g., in camera head 306).

CCU 314 is configured to control various parameters (e.g., activation times, auto exposure, etc.) of image sensors 310. As will be described below, CCU 314 may be further configured to receive and process image data from image sensors 310. While CCU 314 is shown in FIG. 3 to be a single unit, CCU 314 may alternatively be implemented by a first CCU configured to control right-side image sensor 310-R and a second CCU configured to control left-side image sensor 310-L.

Illumination source 316 may be configured to generate and emit illumination 318. Illumination 318 (which is also referred herein to as light) may travel by way of illumination channel 312 to a distal end of shaft 308, where illumination 318 exits to illuminate a scene.

Illumination 318 may include visible or hyperspectral light having one or more frequency (e.g., color) components. Illumination 318 may additionally or alternatively include fluorescence excitation illumination configured to elicit fluorescence illumination by a fluorescence imaging agent (e.g., by exciting a fluorescence imaging agent that has been injected into a bloodstream of a patient to begin emitting fluorescence illumination). In some examples, the fluorescence excitation illumination has a wavelength in an infrared light region (e.g., in a near-infrared light region). While a single illumination source 316 is shown to be included in controller 304, multiple illumination sources each configured to generate and emit differently configured illumination may alternatively be included in controller 304.

To capture one or more images of a scene, controller 304 (or any other suitable computing device) may activate illumination source 316 and image sensors 310. While activated, illumination source 316 emits illumination 318, which travels via illumination channel 312 to the operational area. Image sensors 310 detect illumination 318 reflected from one or more surfaces of anatomy or other objects in the operational area. In cases where illumination 318 includes fluorescence excitation illumination, image sensors 310 may additionally or alternatively detect fluorescence illumination that is elicited by the fluorescence excitation illumination.

Image sensors 310 (and/or other circuitry included in imaging device 302) may convert the sensed light into image data 320 representative of one or more images of the scene. For example, image sensor 310-R outputs image data 320-R representative of images captured from a right-side perspective and image sensor 310-L outputs image data 320-L representative of images captured from a left-side perspective. Image data 320 may have any suitable format.

Image data 320 is transmitted from image sensors 310 to CCU 314. Image data 320 may be transmitted by way of any suitable communication link between image sensors 310 and CCU 314. For example, image data 320 may be transmitted by way of wires included in a cable that interconnects imaging device 302 and controller 304.

CCU 314 may process (e.g., packetize, format, encode, etc.) image data 320 and output processed image data 322 (e.g., processed image data 322-R corresponding to image data 320-R and processed image data 322-L corresponding to image data 320-L). Processed image data 322 may be transmitted to an image processor (not shown), which may prepare processed image data 322 for display on one or more display devices (e.g., in the form of a video stream and/or one or more still images). For example, the image processor may, based on image data 322, generate one or more full color images, grayscale images, and/or fluorescence images for display on one or more display devices.

The images captured and provided by system 300 may be representative of surfaces (e.g., anatomical surfaces, object surfaces, etc.) that are included within a field of view of imaging device 302. For example, a field of view 324 associated with the right side of imaging device 302 is illustrated in FIG. 3. While not explicitly shown, it will be understood that a stereoscopically similar (but not identical) field of view may be associated with the left side of imaging device 302. As such, a field of view of imaging device 302 may refer to either of the right-side or the left-side fields of view, to a field of view representing the overlap of both fields of view, to a field of view representing the combination of both fields of view, or to any other suitable field of view associated with imaging device 302 in a particular implementation.

At any given moment, the extent of the field of view of imaging device 302 may be determined by various factors. For example, the extent of the field of view may incorporate a spatial pose (e.g., a spatial location, spatial orientation, viewing angle, etc.) of the field of view, which may be determined at least partly based on the spatial pose of imaging device 302 itself (and particularly the distal end of imaging device 302).

Additionally, the extent of the field of view may incorporate the shape of the field of view (e.g., which could be rectangular, square, circular, or the like in different implementations), the size or width of the field of view, and other such factors. As will be described in more detail below, these non-pose types of factors may each be defined by one or more parameters associated with imaging device 302. Such parameters may be referred to herein as device-specific parameters (because they are specific to imaging device 302 or to another particular imaging device) and may define any of the following aspects of a particular imaging device.

During an operation performed by medical system 200, imaging device 302 may capture imagery included within a field of view of imaging device 302 (e.g., field of view 324). This imagery may depict an internal view of the body upon which the operation is being performed, and may be provided to team members 210. For instance, the imagery may be provided to clinician 210-1 by way of user control system 204, thereby allowing clinician 210-1 to have visibility into the operational area as the operation is performed using manipulating system 202. Additionally, the imagery may be provided to assistant 210-2 and/or to other team members 210 by way of auxiliary system 206, thereby facilitating these team members in effectively performing their respective tasks. For instance, assistant 210-2 may be responsible for inserting new instruments and/or supplies (e.g., suturing materials, patching materials, etc.) into the operational area where such instruments and supplies may be employed by clinician 210-1 in performing the operations. As such, it may be desirable for assistant 210-2 to easily determine where clinician 210-1 has visibility within the body (e.g., the extent of the field of view of the imaging device providing the imagery of the internal view) so that assistant 210-2 may insert the instruments and/or supplies into the operational area in a manner that is predictable and helpful to the clinician. For example, it may be desirable for assistant 210-2 to insert objects into the field of view where clinician 210-1 will easily be able to see and begin using them, rather than, for example, inserting the objects into a part of the operational area where clinician 210-1 does not have visibility, or into a part of the body that is not necessarily part of the operational area (e.g., behind tissue being operated on, etc.). To this end, system 100 may be configured to present assistant 210-2 with a convenient and easy-to-understand indication of the extent of the field of view using mixed reality technology. Specifically, an external view (e.g., from a vantage point of assistant 210-2 or similar external vantage point providing a view of the body) may be augmented with a shape overlay indicative of the extent of the field of view.

Figure 4:
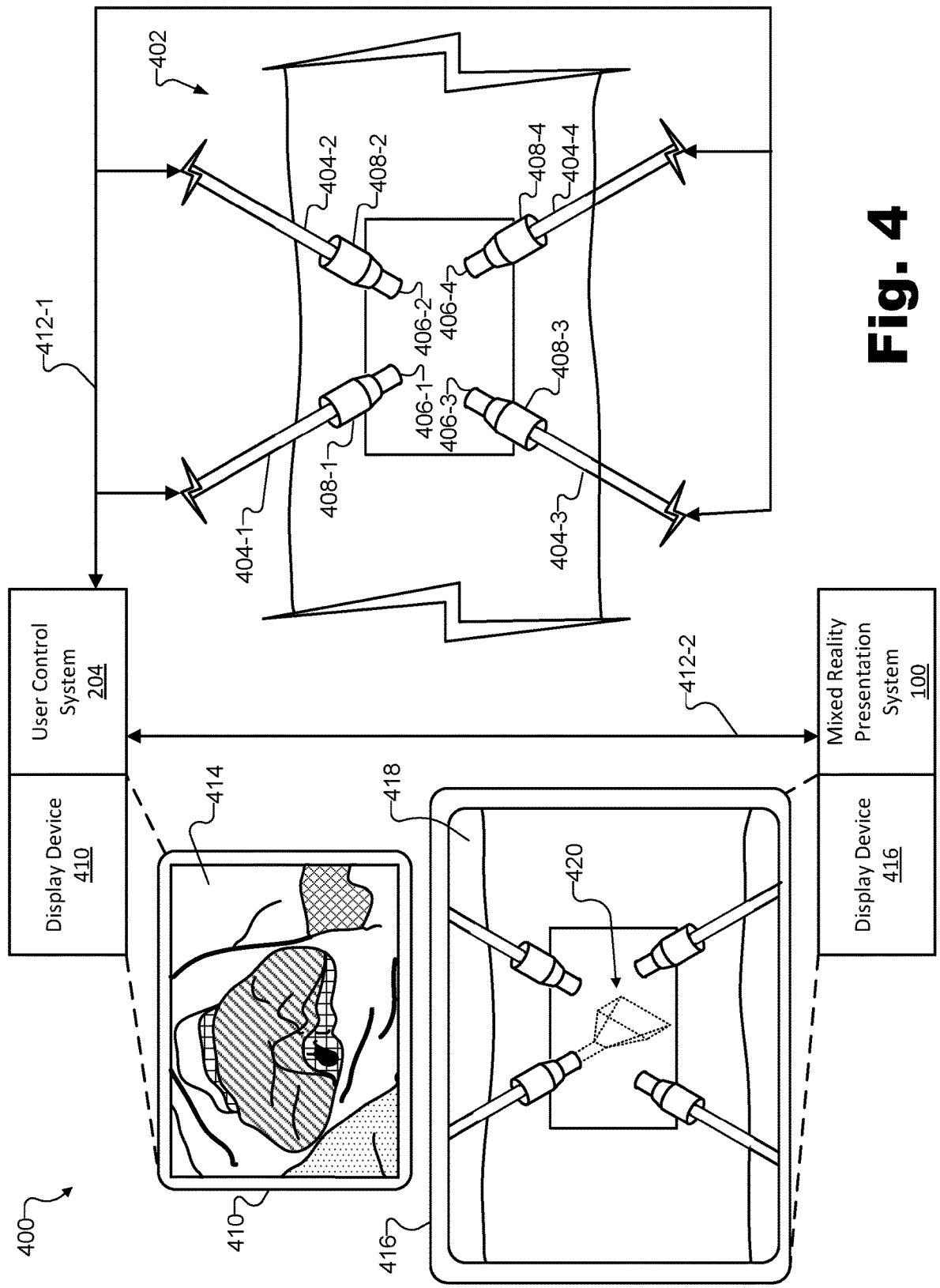
FIG. 4 illustrates an exemplary configuration within which the mixed reality presentation system of FIG. 1 operates to indicate an extent of a field of view of an imaging device according to principles described herein.

To illustrate, FIG. 4 shows an exemplary configuration 400 within which system 100 may operate to indicate an extent of a field of view of an imaging device. Specifically, configuration 400 shows an external view 402 of a body (e.g., a body of a patient or other type of body upon which an operation is being performed as described herein). It will be understood that much of the body may be covered by surgical drapes or the like, but a certain area (e.g., the rectangular area visible in external view 402) may be exposed to allow a plurality of instruments 404 (e.g., instruments 404-1 through 404-4) to be inserted into an operational area internal to the body through a plurality of respective ports 406 (e.g., ports 406-1 through 406-4) and by way of a plurality of respective cannulas 408 (e.g., cannulas 408-1 through 408-4). While not explicitly shown in configuration 400, it will be understood that each instrument 404 may, in certain examples, be coupled to a respective manipulator arm of a manipulating system (e.g., one of manipulator arms 212 of manipulating system 202) as described above with respect to medical system 200.

As described above, medical system 200 may facilitate team members 210 in actively managing (e.g., controlling, etc.) instruments 404 during every phase of an operation performed upon the body using instruments 404. For example, as described above, a display device 410 that is associated with (e.g., integrated into) user control system 204 may be viewed by clinician 210-1 as clinician 210-1 manipulates the manipulator arms to control instruments 404 to thereby perform the operation. As shown, a data communication 412-1 may take place between user control system 204 and each instrument 404. Thus, for example, if instrument 404-1 is an imaging device configured to capture imagery of an internal view of the body, instrument 404-1 may provide data communication 412-1 that is representative of imagery 414 to user control system 204, which, as shown, may be displayed to clinician 210-1 by way of display device 410. While display device 410 illustrates a single (i.e., monoscopic) display depicting imagery 414, it will be understood that, in certain examples, instrument 404-1 may be implemented as a stereoscopic imaging device (e.g., like imaging device 302), and display device 410 may present stereoscopic versions of imagery 414 of the internal view to each eye of clinician 210-1 to allow clinician 210-1 to see the internal view in three dimensions.

In the example of FIG. 4 and other figures described below, instrument 404-1 will be understood to be an imaging device similar or the same as imaging device 302 and, as such, will be referred to as imaging device 404-1. Additionally, within certain contexts described herein, imaging device 404-1 may be understood to be active use for providing imagery during, before, or after an operation such as a medical procedure. Hence, in these contexts, imaging device 404-1 may also be referred to as "active imaging device 404-1."

In this example, other illustrated instruments 404-2 through 404-4 will be understood to be other types of instruments used for manipulating tissue and otherwise performing actions associated with the operation. As such, and as described above, clinician 210-1 may request that assistant 210-2 (or another team member) introduce a particular instrument or a particular object into the operational area by way of a particular port 406 and a particular cannula 408.

However, even if assistant 210-2 can see both external view 402 (i.e., the natural view from the vantage point the assistant has of the body) and imagery 414 of the internal view (e.g., which may be provided not only to display device 410 but also to a display device visible to the assistant such as display monitor 214), it may be difficult to correlate what is seen in the internal and the external views to determine how to effectively introduce the new instrument or object, or to otherwise assist clinician 210-1 (e.g., a surgeon) in a helpful manner. This challenge may be particularly pronounced when imaging device 404-1 supports an angled lens and/or an articulation mechanism allowing the field of view to be angled in various directions away from the axis of the shaft of imaging device 404-1, and/or when imaging device 404-1 is characterized by various other device-specific parameters. Additionally, it may be particularly challenging for assistants to mentally correlate the internal and external views when the vantage point of the assistant is not in line with the imaging device (e.g., when the assistant is viewing the body from an opposite side of the body from the side into which the imaging device is inserted, etc.).

Accordingly, rather than requiring assistant 210-2 to attempt to mentally correlate external view 402 with imagery 414 of the internal view in order to mentally visualize the current position, orientation, shape, and size of the field of view, FIG. 4 shows that system 100 may provide a mixed reality presentation to automatically show assistant 210-2 the extent of the field of view in real time. Specifically, as shown, system 100 may receive a data communication 412-2 from user control system 204 and/or from other sources that may include operating condition data, parameter data, kinematic data, image data, and/or other such data. In response, system 100 may determine that a display device 416 is to toggle (e.g., turn on or turn off) a display of a shape overlay indicative of an extent of a field of view of imaging device 404-1 with respect to external view 402 based on one or more device-specific parameters of imaging device 404-1, the spatial pose of imaging device 404-1, and/or other such information. System 100 may then direct display device 416 to toggle (e.g., begin or cease displaying) a display of a shape overlay presented within a mixed reality presentation 418 to a user of system 100 (e.g., to assistant 210-2 or another such user). As shown, mixed reality presentation 418 may facilitate the user in mentally visualizing the relationship between the view from his or her external vantage point (e.g., external view 402) and the internal view captured by imaging device 404-1 (e.g., depicted by imagery 414) by depicting external view 402 together with a shape overlay 420 that is indicative of the extent of the field of view relative to the body.

Display device 416 may be implemented in any suitable way and/or by any suitable device including a dedicated mixed reality headset device, display monitor 214 associated with auxiliary system 206, display device 410 associated with user control system 204, or the like. Additionally, system 100 and display device 416 may be related to one another in any manner as may serve a particular implementation, such as by display device 416 being integrated into system 100, display device 416 being separate from and communicatively coupled to system 100, or in any other suitable way.

For instance, one exemplary implementation of system 100 may include a mixed reality media player device (e.g., an augmented reality headset) that is configured to be worn on a head of a user. This implementation of system 100 may also include a first physical display included within the mixed reality media player device and configured to provide a graphical presentation to a first eye of the user when the mixed reality media player device is worn on the head of the user and a second physical display configured to provide a graphical presentation to a second eye of the user when the mixed reality media player device is worn on the head of the user. The mixed reality media player device may further include a memory and a processor configured to perform the operations described above as being performed by storage facility 102 and processing facility 104, respectively.

In this example, display device 416 may be collectively implemented by the first and second physical displays included within the mixed reality media player device. As such, rather than the two-dimensional ("2D"), monoscopic mixed reality presentation 418 illustrated in FIG. 4, a 3D, stereoscopic mixed reality presentation 418 may be presented to the user by the first and second physical displays. Regardless of how many separate physical displays are used to implement display device 416, it will be understood that the display device may present a mixed reality (e.g., as opposed to a virtual reality) presentation in the sense that the presentation combines a mix of one or more real elements (e.g., elements visible in external view 402) and one or more virtual elements (e.g., shape overlay 420).

While mixed reality presentation 418 includes a mix of both real and virtual elements, it will be understood that the real and virtual elements may be presented in different ways. For example, in certain implementations, a camera associated with system 100 may provide a photographic rendering of external view 402 that the virtual elements may be combined with and presented to the user on a standard (i.e., opaque) screen.

In other examples, system 100 may employ one or more see-through displays upon which the virtual elements are presented in front of (e.g., overlaid onto) a direct view of the real external view. For example, the first physical display in the implementation of system 100 described above may be a first see-through display configured to provide, in the graphical presentation to the first eye of the user, a first combination of: 1) imagery of external view 402 of the body provided by light passing through the first see-through display, and 2) a first depiction of shape overlay 420 provided by light generated by the first see-through display to display shape overlay 420 together with external view 402 for the first eye. Similarly, the second physical display in this implementation of system 100 may be a second see-through display configured to provide, in the graphical presentation to the second eye of the user, a second combination of: 1) the imagery of external view 402 of the body provided by light passing through the second see-through display, and 2) a second depiction of shape overlay 420 provided by light generated by the second see-through display to display shape overlay 420 together with external view 402 for the second eye.

Other exemplary implementations of system 100 may not include or be associated with a mixed reality media player device worn by the user. Rather, these exemplary implementations may include, for example, a mixed-reality-enabled display monitor device (e.g., implemented by display monitor 214 of auxiliary system 206) that is configured for viewing by a user without being worn by the user. This implementation of system 100 may also include a physical display included within the mixed-reality-enabled display monitor device and configured to display a combination of 1) imagery of the external view of the body captured by a camera located at a vantage point associated with external view 402 of the body, and 2) a depiction of shape overlay 420 generated by the physical display. The mixed-reality-enabled display monitor device may further include a memory and a processor configured to perform the operations described above as being performed by storage facility 102 and processing facility 104, respectively. In this example, display device 416 may be implemented by the physical display included within the mixed-reality-enabled display monitor device.

When toggled on to begin being displayed, shape overlay 420 may be displayed together with external view 402 in a manner that integrates shape overlay 420 with the objects included in the external view. Put another way, shape overlay 420 may be displayed within mixed reality presentation 418 in a manner that augments external view 402 in accordance with established mixed reality techniques and technologies. To this end, as shown in the example of mixed reality presentation 418, system 100 may direct display device 416 to display shape overlay 420 together with external view 402 by directing display device 416 to display shape overlay 420 overlapping external view 402 such that a shape depicted in shape overlay 420 appears to be integrated with one or more objects visible in external view 402.

Shape overlay 420 may include one or more virtual objects and/or other augmentations configured to be displayed together with real imagery in mixed reality presentation 418. As such, shape overlay 420 may be implemented in any suitable way such as, for example, by depicting a 3D geometric shape having a form of a rectangular pyramid, a rectangular frustum, a circular cone, a circular frustum, or any other 3D geometric shape as may serve a particular implementation. In other examples, shape overlay 420 may depict a 2D shape corresponding to any one of these 3D shapes, or may depict another 2D shape, 3D shape, or other such augmentation as may serve a particular implementation. As will be described and illustrated in more detail below, a shape overlay may further depict other objects along with depicting a shape. For example, such objects may include a representation of a distal end of an imaging device, a portion of a cannula or other hardware associated with a port, a simulated depiction of an internal area within the body, or any other such object as may serve a particular implementation.

Shape overlay 420 may be rendered in various ways to conveniently indicate various types of information to a user (e.g., a viewer of mixed reality presentation 418 on display device 416), or to otherwise facilitate indicating the extent of the field of view of imaging device 404-1.

To illustrate, FIGS. 5A through 5I illustrate various exemplary shape overlays 500 (i.e., shape overlays 500-A through 500-I shown in FIGS. 5A through 5I, respectively) that may be displayed by a display device as directed by an implementation of system 100. Each of shape overlays 500 may represent a particular implementation of shape overlay 420 (or a portion thereof) that may be displayed on a display device (e.g., display device 416) and that may be based on certain settings (e.g., user preferences, etc.) of system 100.

While shape overlays 500-A through 500-I primarily illustrate respective shapes that may be depicted in exemplary shape overlays, it will be understood that other objects not shown in shape overlays 500-A through 500-I (e.g., virtual representations of a distal end of an imaging device, etc.) may further be depicted in various shape overlays. Examples of such objects will be illustrated in more detail below.

Figure 5A:
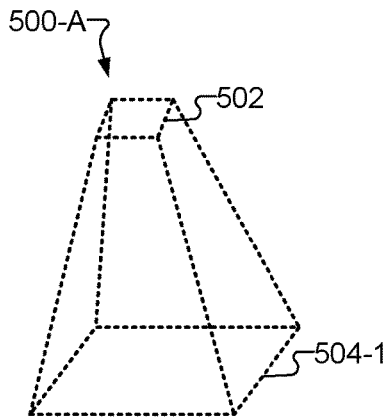
FIGS. 5A-5I illustrate various exemplary shape overlays and aspects thereof that may be displayed by a display device as directed by the mixed reality presentation system of FIG. 1 according to principles described herein.

FIG. 5A shows shape overlay 500-A, which depicts a 3D rectangular frustum shape having a face of origination 502 that corresponds to the location of the imaging device, as well as a base 504-1 that is presented opposite the location of the imaging device. As shown, shape overlay 500-A depicts a rectangular frustum shape in wireframe form such that all of the edges of the shape are visible. Additionally or alternatively, shape overlay 500-A may be understood to depict a shape that is at least partially transparent, thereby allowing all of the edges and faces of the shape to be visible.

Figure 5B:
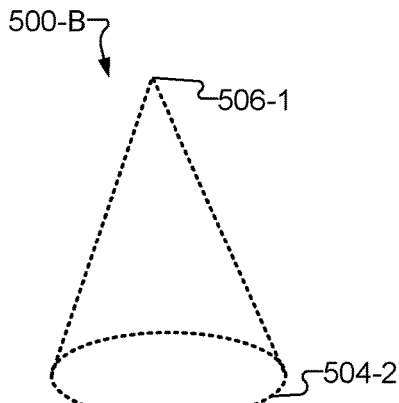

FIG. 5B shows shape overlay 500-B, which depicts a 3D cone shape having a point of origination 506-1 that corresponds to the location of the imaging device. As shown, shape overlay 500-B also includes a base 504-2 that, like base 504-1, is presented opposite the location of the imaging device.

Figure 5C:
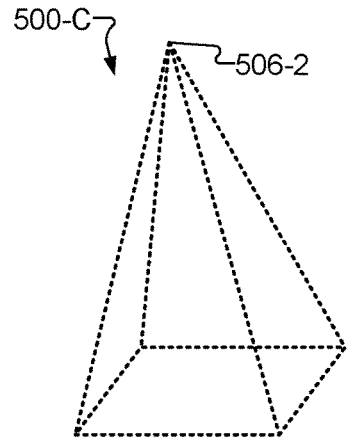

FIG. 5C shows shape overlay 500-C, which depicts a 3D pyramid shape that is similar to the frustum depicted in shape overlay 500-A but, instead of a face of origination such as face 502, includes a point of origination 506-2. It will be understood that, as mentioned above, other geometric shapes (e.g., 2D geometric shapes, 3D geometric shapes, etc.) may similarly be depicted by a shape overlay. For instance, a shape overlay may depict a 3D circular frustum having a face of origination, or any other suitable 3D or 2D shape.

Figure 5D:
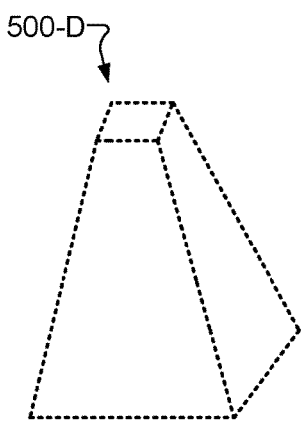

FIG. 5D shows shape overlay 500-D, which, in contrast to the wireframe and/or transparent shapes depicted in other examples, depicts an opaque (i.e., non-transparent) rectangular frustum. Any degree of transparency and/or manner of construction (e.g., line style, color, texture, etc.) of the shapes depicted in shape overlays 500 may be employed as may serve a particular implementation or, in certain examples, as may be preferred by a particular user.

Figure 5E:
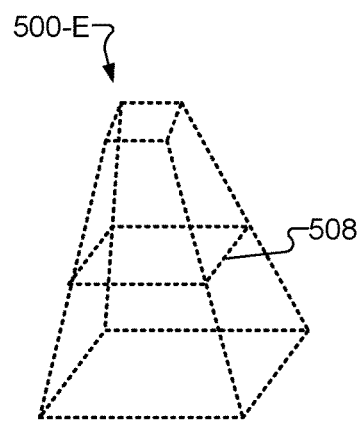

FIG. 5E shows shape overlay 500-E, which depicts a shape that not only includes a face of origination and a base similar to shapes depicted in other shape overlays 500 described above, but further includes a cross section 508. As shown, cross section 508 is shown to be parallel to, yet distinct from, the face of origination and the base. Cross section 508 may be used to illustrate various image device characteristics such as a focus depth of the imaging device (e.g., a nominal focus depth, a current focus depth, etc.). Any information that may be indicated by a base of a shape depicted in a shape overlay (e.g., tissue depth or the like) may alternatively be indicated by a cross section 508 that is distinct from the base.

Figure 5F:
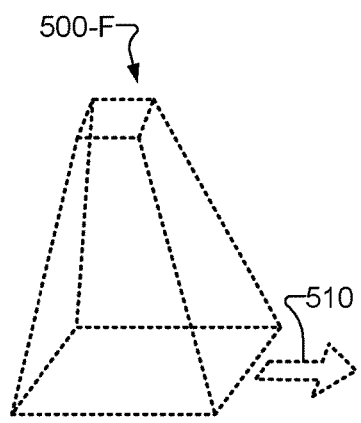

FIG. 5F shows shape overlay 500-F, which depicts not only a 3D frustum shape, but also an indicator arrow 510 that indicates an orientation of the field of view represented by the frustum shape. Indicator arrow 510 may be configured to indicate, for instance, which side of the base of the frustum corresponds to a top side of imagery provided by the imaging device (e.g., a top side of imagery 414 in FIG. 4). In other examples, rather than an indicator arrow, the orientation may be indicated in other ways such as by depicting a dot or other such marker at a particular corner or side of the base of the frustum (e.g., a dot to indicate the top-left corner of the imagery, etc.), showing a particular side with a particular color, including text within the shape overlay, depicting an icon or avatar representative of clinician 210-1 to show the orientation at which clinician 210-1 is viewing the imagery in the field of view, or any other way as may serve a particular implementation.

Figure 5G:
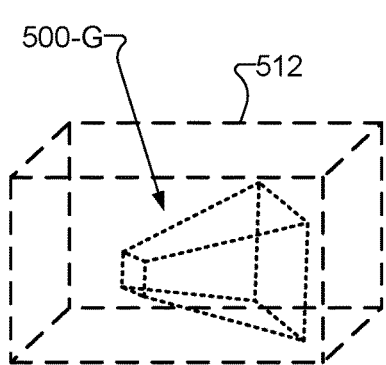

FIG. 5G shows shape overlay 500-G, which is depicted together with a simulated depiction 512 of an internal portion of a body. As shown, simulated depiction 512 may be displayed together with shape overlay 500-G and with the external view of the body, and may be made to appear to be behind the shape overlay (e.g., between the real elements of the external view and the shape overlay). In some examples, part of simulated depiction 512 may also be displayed so as to appear to be in front of shape overlay 500-G, such that the shape overlay appears to be contained inside of the simulated depiction, just as the shape overlay is meant to appear to be contained inside the body. For instance, as shown, simulated depiction 512 may appear to surround shape overlay 500-G, thereby making it easier for a viewer to visualize that shape overlay 500-G is actually inside the body with the imaging device (rather than merely overlaid onto the external view of the body). In certain examples, a simulated depiction of an internal portion of the body may also include a depiction of other elements such as a virtual port, a virtual cannula, or the like, whereby the imaging device is inserted into the body.

Figure 5H:
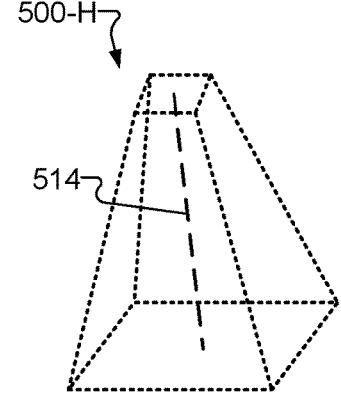

FIG. 5H shows shape overlay 500-H, which includes an image capture axis 514 indicative of a center of the imagery being captured by the imaging device. Image capture axis 514 may indicate, for example, an area of focus that clinician 210-1 may be currently concerned with more than other areas within the field of view of imaging device 404-1.

Figure 5I:
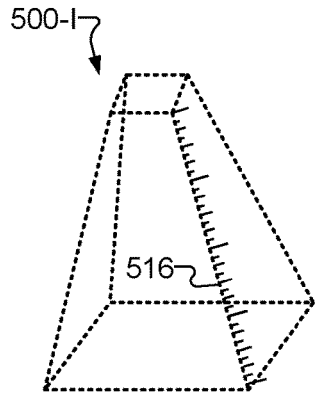

FIG. 5I shows shape overlay 500-I, which includes a ruler 516 indicative of a distance from the face of origination (i.e., a distance from the imaging device) to a base or cross section of the shape. While ruler 516 is shown to be drawn along an edge of the geometric shape in shape overlay 500-I, it will be understood that ruler 516 may, in other examples, be drawn along an image capture axis such as image capture axis 514, along a different dimension (e.g., any of an x, y, or z dimension), of the like.

The features described with respect to shape overlays 500-A through 500-I are exemplary only. In other shape overlays, any of the features described above, any other suitable features, or any combination thereof, may also be employed. In some examples, a shape overlay may additionally or alternatively indicate different types of information by including different colors, line styles, shading styles, degrees of transparency, textual annotations, graphical icons, and so forth. These or other features may be used to indicate, for instance, that a problem has been encountered (e.g., an imaging device failure, an illuminator failure, fogging or debris detected on a lens of the imaging device, a focusing issue, etc.), that a particular mode of the imaging device (e.g., associated with a particular imaging technology, capture frequency, etc.) is being used, that the imaging device has been detected to collide with another instrument, that clinician 210-1 has requested a different imaging device be inserted as the active imaging device, and/or to any other information that may be of interest to user of system 100.

Additionally, it will be understood that various other types of useful information may also be presented in conjunction with any of the shape overlays described herein. For instance, in certain examples, a shape overlay may further provide additional perspective to a user viewing the shape overlay by superimposing an image captured by the imaging device (e.g., a live, real-time video image or a previous still image corresponding to imagery 414) onto a base or cross-section of the shape overlay.

Figure 6:
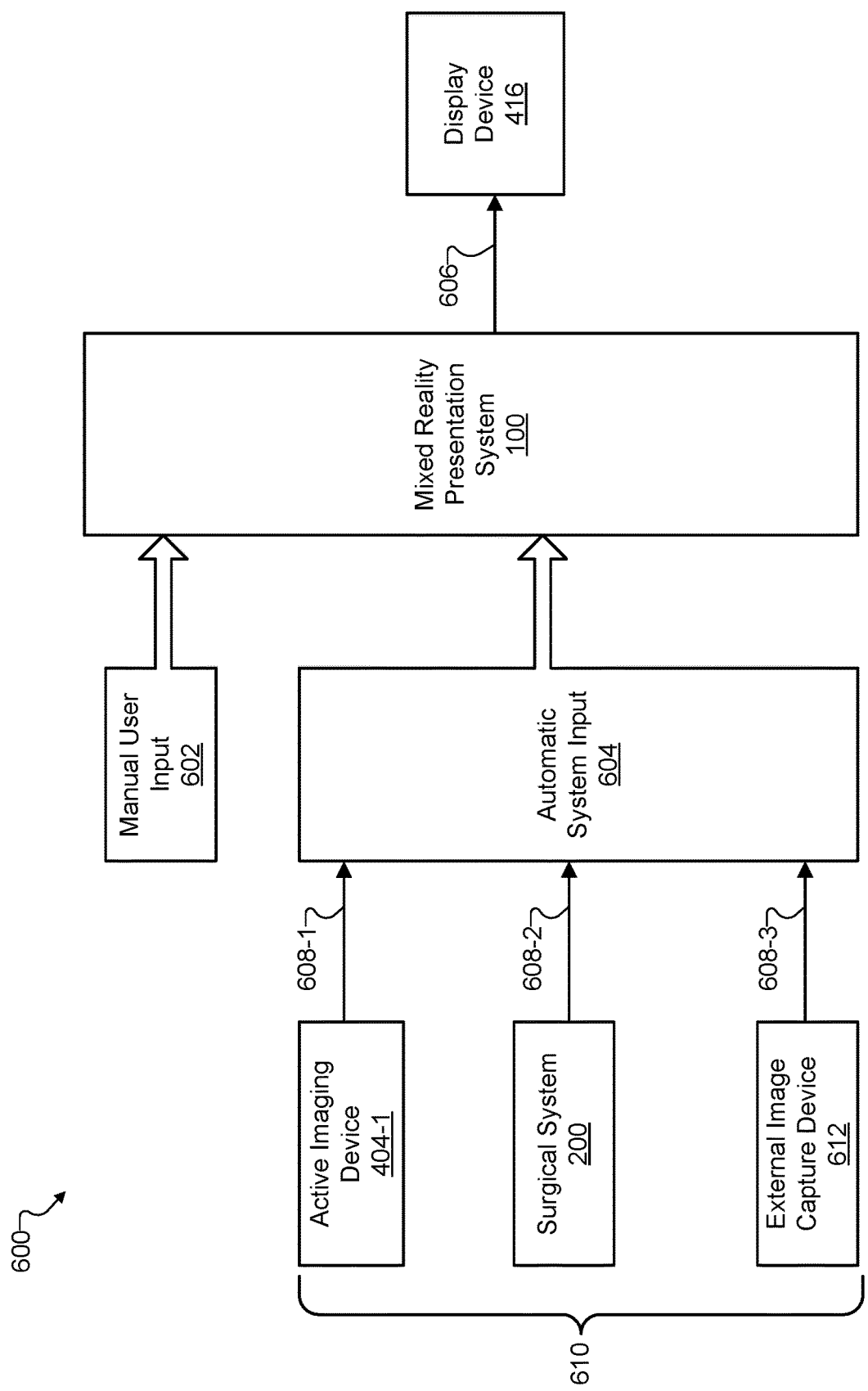
FIG. 6 illustrates an exemplary functional dataflow by way of which the mixed reality presentation system of FIG. 1 may toggle a display of a shape overlay that is indicative of an extent of a field of view of an imaging device according to principles described herein.

FIG. 6 shows another exemplary configuration 600 within which system 100 may operate to indicate an extent of a field of view of an imaging device. In contrast to configuration 400, which, as described above, graphically illustrates how system 100 interrelates with external and internal views of a body, configuration 600 illustrates, with more particularity, various data that may be input to and output from system 100. Specifically, as shown in configuration 600, system 100 may receive manual user input 602 and/or automatic system input 604, and, after analyzing and processing either or both of these inputs (as well as other input data in certain examples), may provide shape overlay data 606 to display device 416. Each of the elements of configuration 600 will now be described in more detail.

Manual user input 602 may represent any suitable type of user input data that may be manually provided to system 100 by any user of system 100 as may serve a particular implementation. As described above, a user of system 100 may be a team member 210 such as clinician 210-1, assistant 210-2, or another team member who may be viewing display device 416 and may desire to control the display of the shape overlay on display device 416 (e.g., controlling the toggling on and off of the display and/or other aspects of the display). In various examples, manual user input 602 may include input received by way of user manipulation of a physical user interface element (e.g., a physical button, switch, foot pedal, etc.), a digital user interface element implemented by a touch screen or the like (e.g., a digital button or switch, a textual command interface, etc.), or another suitable type of user interface (e.g., a gesture-based user interface, a voice-controlled user interface, etc.). In some of these examples, user input may be provided intentionally (e.g., by the user pressing a button to toggle the display of the shape overlay), while, in other examples, user input may be provided incidentally or unintentionally (e.g., by the user turning his or her head to look in a particular direction such as toward the body or toward display device 416).

In any of these examples, system 100 may allow the user to manually direct the toggling of the display of the shape overlay at will by way of any of the user interfaces described above. Additionally or alternatively, system 100 may automatically direct the toggling of the display of the shape overlay based on automatic system input 604 that is representative, as mentioned above, of one or more operating conditions associated with an operation (e.g., a medical procedure, etc.) performed on the body. As will be described in more detail below, such operating conditions will be understood to broadly include various conditions associated with the operation. However, it will also be understood that operating conditions, as used herein, do not include direct, manual user input provided by a user to manually toggle the display of the shape overlay (e.g., manual user input 602).

Rather, as shown in configuration 600, automatic system input 604 may include various instances of automatic input data 608 (e.g., input data 608-1 through 608-3) which may be directly representative of one or more operating conditions associated with the operation performed on the body, or may include data from which one or more such operating conditions may be derived. Each instance of input data 608-1 through 608-3 may be provided automatically by a particular data source 610 such as active imaging device 404-1, medical system 200 (e.g., other components of medical system 200 besides active imaging device 404-1), an external image capture device 612, and/or any other suitable data source as may serve a particular implementation.

Input data 608 may represent operating conditions (or be used to derive operating conditions) that system 100 employs when automatically determining that display device 416 is to toggle a display of a shape overlay. While such operating conditions are provided automatically by respective data sources 610 (or derived from information provided automatically by these data sources), rather than provided by manual input from a user, it will be understood that system 100 may still receive, derive, and/or use the operating conditions in accordance with system settings that have been manually selected by a user. For example, a user may configure settings of system 100 to enable automatic toggling of the display of the shape overlay in response to certain operating conditions in certain contexts, while not enabling automatic toggling of the display in response to other operating conditions and/or in other contexts.

Various suitable operating conditions employed by system 100 to determine that the display of a shape overlay is to be toggled may be represented by and/or derived from input data 608. In some examples, system 100 may determine that the display of the shape overlay is to be toggled based on a combination of such operating conditions. System 100 may identify (e.g., receive, derive, etc.) such operating conditions in any manner as may serve a particular implementation.

For instance, as one example, system 100 may identify an operating condition by detecting a position of a distal end of active imaging device 404-1 in relation to an internal area of the body from which the active imaging device captures the imagery of the internal view. It may not be particularly useful or desirable for the display of the shape overlay to be enabled while the distal end of active imaging device 404-1 is positioned external to the body (e.g., because the distal end may be viewed directly by the user from the external view). Similarly, it may also not be particularly desirable for the display of the shape overlay to be enabled as the distal end of active imaging device 404-1 is being inserted through cannula 408-1 (e.g., because the field of view of the active imaging device will be very limited inside cannula 408-1). However, when the distal end emerges from cannula 408-1 into the internal area of the body, it may be desirable for the shape overlay to be displayed to indicate the extent of the field of view while the distal end of active imaging device 404-1 is occluded from the external view. Accordingly, system 100 may automatically determine that display device 416 is to enable (i.e., toggle on) the display of the shape overlay based on detecting that the distal end has arrived into the internal area of the body. Similarly, system 100 may automatically determine that display device 416 is to disable (i.e., toggle off) the display of the shape overlay based on detecting that the distal end has exited the internal area (e.g., when the distal end is being withdrawn out of cannula 408-1, etc.).

As another example, system 100 may identify an operating condition by detecting an operational status of a component associated with active imaging device 404-1. The operational status may relate, for instance, to whether the component is powered on and/or is operating properly. For example, system 100 may detect the operational status of an image sensor included in active imaging device 404-1, a communication link by way of which active imaging device 404-1 provides data associated with the imagery of the internal view, a light source associated with active imaging device 404-1 and configured to illuminate the internal area of the body from which active imaging device 404-1 captures the imagery, and/or any other such component associated with active imaging device 404-1. In some cases, it may be useful and desirable for the display of the shape overlay to be enabled only if each of these components of active imaging device 404-1 are powered on and operating properly. Accordingly, system 100 may automatically determine that display device 416 is to enable the display of the shape overlay based on the detected operational status of one or more of the components of active imaging device 404-1 (e.g., based on detecting that the components are powered on and/or operating properly). Similarly, system 100 may automatically determine that display device 416 is to disable the display of the shape overlay based on the detected operational status of the components (e.g., based on detecting that one or more of the components has been powered off or is malfunctioning).

As yet another example, system 100 may identify an operating condition by determining a status of an object insertion process in which an object is inserted into an internal area of the body. One purpose of displaying the shape overlay may relate to facilitating an insertion, by a user (e.g., assistant 210-2), of an instrument or other object into a field of view of the active imaging device (e.g., the field of view visible to clinician 210-1 during the operation). Accordingly, it may be useful and desirable for the display of the shape overlay to be enabled while an object insertion process is ongoing, while it may be less useful (or, in some cases, distracting or otherwise undesirable) for the display of the shape overlay to be enabled at other times such as after the object insertion process is complete. As such, system 100 may automatically determine that display device 416 is to enable the display of the shape overlay when the status of the object insertion process is determined to be ongoing.

Similarly, in certain examples, system 100 may also automatically determine that display device 416 is to disable the display of the shape overlay when the determined status of the object insertion process indicates that the process is complete (e.g., that the instrument or other object has been successfully inserted). For example, the determining of the status of the object insertion process may include detecting that the instrument or other object is visible within the field of view. As such, the directing of display device 416 to toggle the display of the shape overlay may include directing display device 416 to cease displaying the shape overlay based on the detection that the object is visible within the field of view. In this way, the user may automatically see the display of the shape overlay when the display is helpful and useful, while not being distracted by the display after the usefulness of the display concludes.

Each instance of input data 608 may include any suitable data that is representative of any of the operating conditions described herein or from which such operating conditions may be derived. As shown, each instance of input data 608 may be transmitted by a different data source 610. It will be understood that any or all of input data 608, as well as data determined therefrom, may collectively form automatic system input 604 input into system 100.

The different instances of input data 608, as well as the data sources 610 that provide this data, will now be described. While the primary focus of this description is related to operating conditions used by system 100 to determine when to toggle the display of the shape overlay, it will be understood that the same data 608, as well as other additional data (e.g., data from the same and/or other data sources and which may not be explicitly shown or described herein), may also be provided and used to determine how to display the shape overlay. For example, based on data from data sources 610, system 100 may determine a spatial pose of active imaging device 404-1 (e.g., including where active imaging device 404-1 is located in space, how active imaging device 404-1 is oriented in space, etc.), one or more device-specific parameters associated with active imaging device 404-1 (e.g., parameters affecting a shape and/or other aspects of the field of view of active imaging device 404-1), and other information relevant to the real-time extent of the field of view of active imaging device 404-1. Based on this data, system 100 may determine an extent of the field of view of active imaging device 404-1 relative to the body. More specifically, system 100 may determine the shape, zoom level, current angle, current width, etc., of the field of view, and may determine where active imaging device 404-1 is located in relation to the body. To this end, system 100 may be configured to correlate the external view and the shape overlay using any suitable registration techniques and/or technologies (e.g., including calibration techniques; image processing techniques; Simultaneous Localization and Mapping ("SLAM") technologies; marker-based, marker-less, and/or vision-based techniques, a combination of any of these, etc.).

In addition to determining the spatial relationship between the position of the imaging device and the position of the body, system 100 may further be configured to determine a spatial relationship between the position and/or orientation of the field of view of the imaging device and the position and/or orientation of the image display of the display device by way of which the external view and the shape overlay are presented to the user. As with the spatial relationship between the imaging device and the body, the spatial relationship between the field of view of the imaging device and the image display of the display device may be determined in any suitable way and using any registration techniques and/or technologies described herein. For example, system 100 may determine the position and/or orientation of the field of view of the imaging device by determining the position and/or orientation of a part of the imaging device and accessing information describing the geometry of the spatial relationship between the field of view of the imaging device and that part of the imaging device. As another example, system 100 may determine the position and/or orientation of the field of view of the image display of the display device by determining the position and/or orientation of a part of the display device and accessing information describing the geometry of the spatial relationship between the image display of the display device and that part of the display device.

Thus, for instance, in some examples, system 100 may determine the spatial relationship between the positions and/or orientations of the display device and the imaging device using a direct spatial transform between the respective positions and/or orientations of the display device and the imaging device. In other examples, system 100 may determine the spatial relationship using a series of transforms linking the respective positions and/or orientations. For example, one series of transforms may include a first transform from the position and/or orientation of the display device to the position and/or orientation of the body, and a second transform from the position and/or orientation of the body to the position and/or orientation of the imaging device. As another example, a series of transforms may include a first transform from the position and/or orientation of the display device to a particular component of a manipulating system, and one or more additional transforms from the particular component of the manipulating system through various links and joints of the manipulating system (e.g., one or more links or joints of a manipulator arm included in the manipulating system) to the position and/or orientation of the imaging device. Any of these transforms or other suitable transforms may be derived based on kinematic data, visual or non-visual data based on passive or active markers or indicia, or using any other data, technique, or technology described herein or as may serve a particular implementation.

Input data 608-1 may include state data representative of information about active imaging device 404-1 and/or operational statuses of components of active imaging device 404-1. For example, input data 608-1 may include data representative of the operational status of one or more image sensors included within active imaging device 404-1, a communication link used by active imaging device 404-1, a light source associated with active imaging device 404-1, or the like. As another example, input data 608-1 may include data from which may be determined the status of an object insertion process. For instance, input data 608-1 may include imagery data captured by active imaging device 404-1 (e.g., imagery data 412). Based on such imagery data and/or other data received from other data sources 610, system 100 may use machine learning or other suitable techniques to determine the status of the object insertion process (e.g., to determine that the process is still ongoing, to determine that the process has been successfully completed, etc.). As described above, any of these types of input data 608-1 may be used to represent or derive an operating condition that system 100 may use to determine whether to toggle the display of the shape overlay.

Input data 608-2 may include kinematic data representative of (or from which may be derived) a position of a distal end of active imaging device 404-1 in relation to an internal area of the body. As such, input data 608-2 may be used to determine when the distal end has been inserted through the cannula to emerge into the internal area, when the distal end has been withdrawn back into the cannula to be pulled out of the internal area, or the like. As described above, medical system 200 may provide kinematic data or other types of data indicative of the spatial pose of active imaging device 404-1 or otherwise characterizing or defining the extent of the field of view. In some examples, kinematic data included in input data 608-2 may indicate the spatial pose of imaging device 404-1 (e.g., the distal end of imaging device 404-1) by indicating an updated spatial position of imaging device 404-1, an updated orientation of imaging device 404-1 (e.g., including a direction in which an angled lens of imaging device 404-1 is facing), an updated articulation configuration of imaging device 404-1, or the like. As described above, any of these types of input data 608-2 may be used to represent or derive an operating condition that system 100 may use to determine whether to toggle the display of the shape overlay.

Input data 608-3 may include photographic data captured from an external view of the body, and that may be used, in addition or as an alternative to the types of data included in input data 608-1 and 608-2, for determining one or more of the operating conditions described herein. For example, input data 608-3 may include photographic data that indicates a real time position of markers associated with active imaging device 404-1, thereby allowing system 100 to determine, based on the positioning of the markers, that spatial pose of active imaging device 404-1 at a particular moment in time. Such data may also indicate if active imaging device 404-1 is being inserted or withdrawn from the cannula, how deeply active imaging device 404-1 is inserted within the body, where the user is in relation to display device 416 (e.g., to indicate if user is close enough to display device 416 that the shape overlay will be visible and useful if enabled), and so forth. External image capture device 612 may be implemented by a video camera or other type of external image capture device to provide photographic imagery of the external view and/or imagery included within input data 608-3.

Based on manual user input 602 and/or automatic system input 604, system 100 may determine when the display of the shape overlay is to be toggled and, in response, may direct display device 416 to toggle the display by way of shape overlay data 606. For example, when system 100 determines that the display of the shape overlay is to be toggled on, system 100 may direct display device 416 to begin displaying the shape overlay by generating and providing (e.g., transmitting) shape overlay data 606 to display device 416. As shown, system 100 may receive shape overlay data 606 from system 100 and may use shape overlay data 606 to display the shape overlay together with the external view. Specifically, based on shape overlay data 606, display device 416 may display the shape overlay to indicate the extent of the field of view relative to the body, including the proper position of the field of view, the proper shape and size of the field of view, and so forth. Conversely, when system 100 determines that the display of the shape overlay is to be toggled off, system 100 may direct display device 416 to cease displaying the shape overlay by ceasing the generation and/or transmission of shape overlay data 606 to display device 416.

As has been described, system 100 may direct a display device to toggle a display of a shape overlay of an active imaging device for various reasons (e.g., based on both manual user input and automatic system input). When the display of the shape overlay is enabled to indicate the current field of view of the active imaging device in the appropriate context, the shape overlay may help provide various types of useful information to a user, as has been described. In some examples, however, rather than showing (or only showing) the shape overlay corresponding to the current field of view, it may be desirable to show a second shape overlay for a field of view distinct from the current field of view (e.g., instead of or in addition to the shape overlay associated with the current field of view). Such a second or additional shape overlay may be referred to herein as an auxiliary shape overlay.

In some cases, a user of system 100 may provide user input requesting to view an auxiliary shape overlay together with or instead of the standard shape overlay (i.e., the shape overlay corresponding to the current field of view of the active imaging device). In other cases, system 100 may automatically determine that it would be useful or desirable for the user to be presented with the auxiliary shape overlay in addition or as an alternative to the standard shape overlay. Regardless, system 100 may be configured to direct a display device to display both the standard shape overlay and the auxiliary shape overlay concurrently or one at a time for any suitable purpose. This may be beneficial for various reasons. For example, by displaying an auxiliary shape overlay indicative of a potential field of view in conjunction with the displaying of the shape overlay indicative of the current field of view, a user may be able to quickly see and understand important information with minimal mental visualization.

A potential field of view to which an auxiliary shape overlay may correspond may be implemented by any potential field of view of any suitable imaging device as may serve a particular implementation. For instance, in some examples, a potential field of view may be associated with an imaging device other than the active imaging device currently in use. Specifically, for example, system 100 may determine that display device 416 is to display an auxiliary shape overlay together with the external view of the body. The auxiliary shape overlay may be indicative of an extent (e.g., relative to the body) of a potential field of view of an auxiliary (e.g., non-active) imaging device that is distinct from the active imaging device. For example, the auxiliary imaging device may be an available imaging device that has different parameters or uses a different imaging technology than active imaging device 404-1, and may be selected for use because it is anticipated that the auxiliary imaging device may be able to achieve a field of view that is not possible or convenient to achieve with active imaging device 404-1. As such, based on the determining that display device 416 is to display the auxiliary shape overlay, system 100 may direct display device 416 to display the auxiliary shape overlay together with the external view of the body (e.g., together with or in place of the standard shape overlay).

In other examples, a potential field of view may be associated with the active imaging device (e.g., active imaging device 404-1). Specifically, for instance, system 100 may determine that display device 416 is to display an auxiliary shape overlay together with the external view of the body. The auxiliary shape overlay may be indicative of an extent (e.g., relative to the body) of a potential field of view of the active imaging device. However, the potential field of view may be distinct from the current field of view indicated by the standard shape overlay. As such, based on the determining that display device 416 is to display the auxiliary shape overlay, system 100 may direct display device 416 to display the auxiliary shape overlay together with the external view of the body (e.g., together with or in place of the standard shape overlay).

To illustrate, FIGS. 7-10 show display device 416 displaying different exemplary shape overlays together with an exemplary external view of a body according to principles described herein. Specifically, each of FIGS. 7-10 illustrate a standard shape overlay associated with the current field of view of the active imaging device 404-1 together with an auxiliary shape overlay associated with a potential field of view of either active imaging device 404-1 or another imaging device (e.g., a non-active imaging device that may be available for use during the operation).

Each of FIGS. 7-10 depict display device 416 presenting mixed reality presentation 418. As described above, mixed reality presentation 418 includes real elements of an external view of a body combined with virtual elements displayed by display device 416. As shown in each of FIGS. 7-10, for instance, mixed reality presentation 418 combines real elements of external view 402 with virtual elements of a shape overlay (e.g., an implementation of shape overlay 420). For example, real elements viewable in external view 402 include, without limitation, an external surface of the body (e.g., skin, surgical drapes, etc.), an external portion of active imaging device 404-1, an external portion of cannula 408-1 at port 406-1, and so forth. As shown in FIGS. 7-10, each of the real elements included in external view 402 are depicted with solid lines. As described above, these real elements may be presented on display device 416 based on real-time photographic imagery, directly through a see-through display or in any other suitable way.

Figure 7:
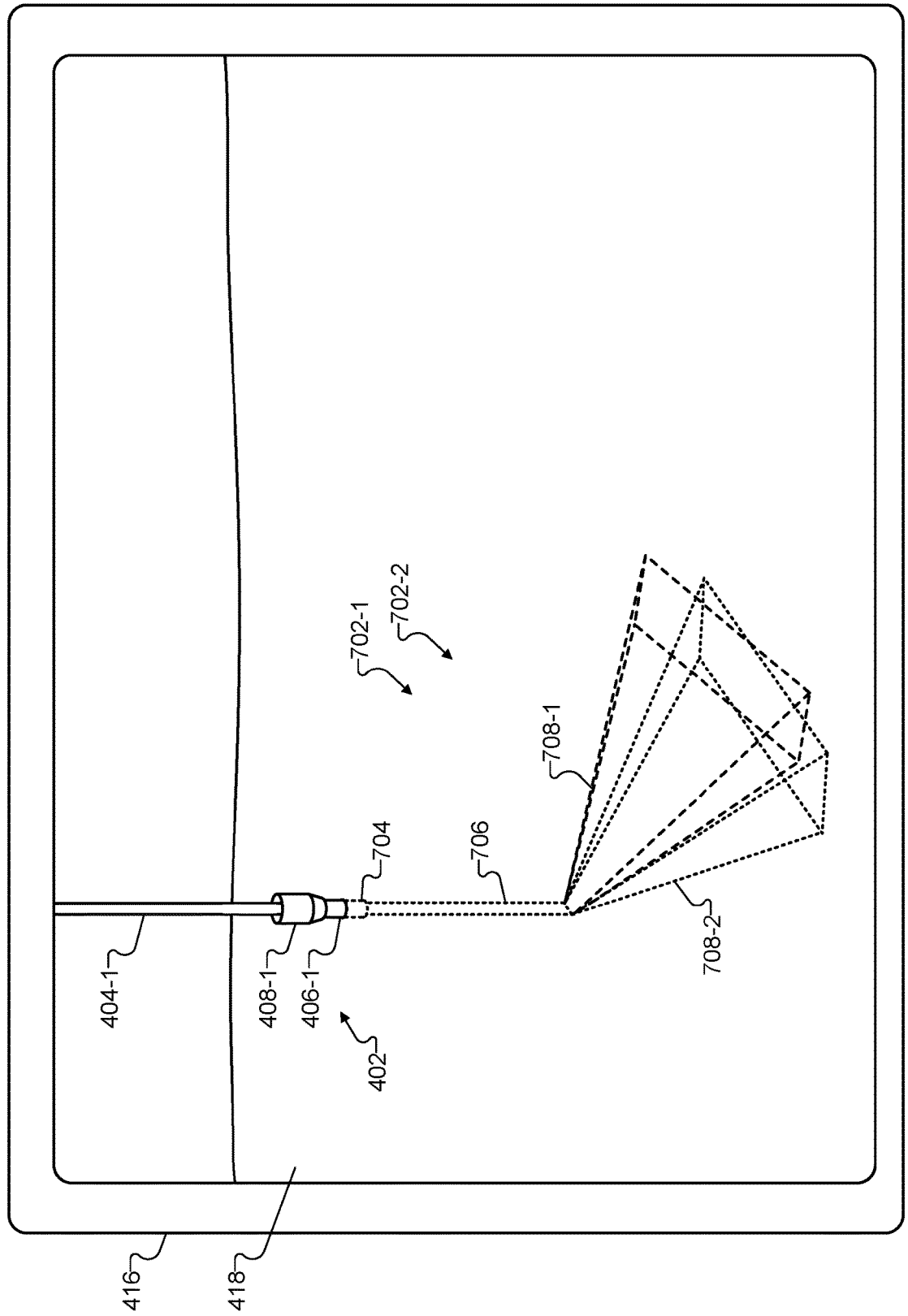
FIGS. 7-10 illustrate an exemplary display device displaying different exemplary shape overlays together with an exemplary external view of a body according to principles described herein.
Figure 8:
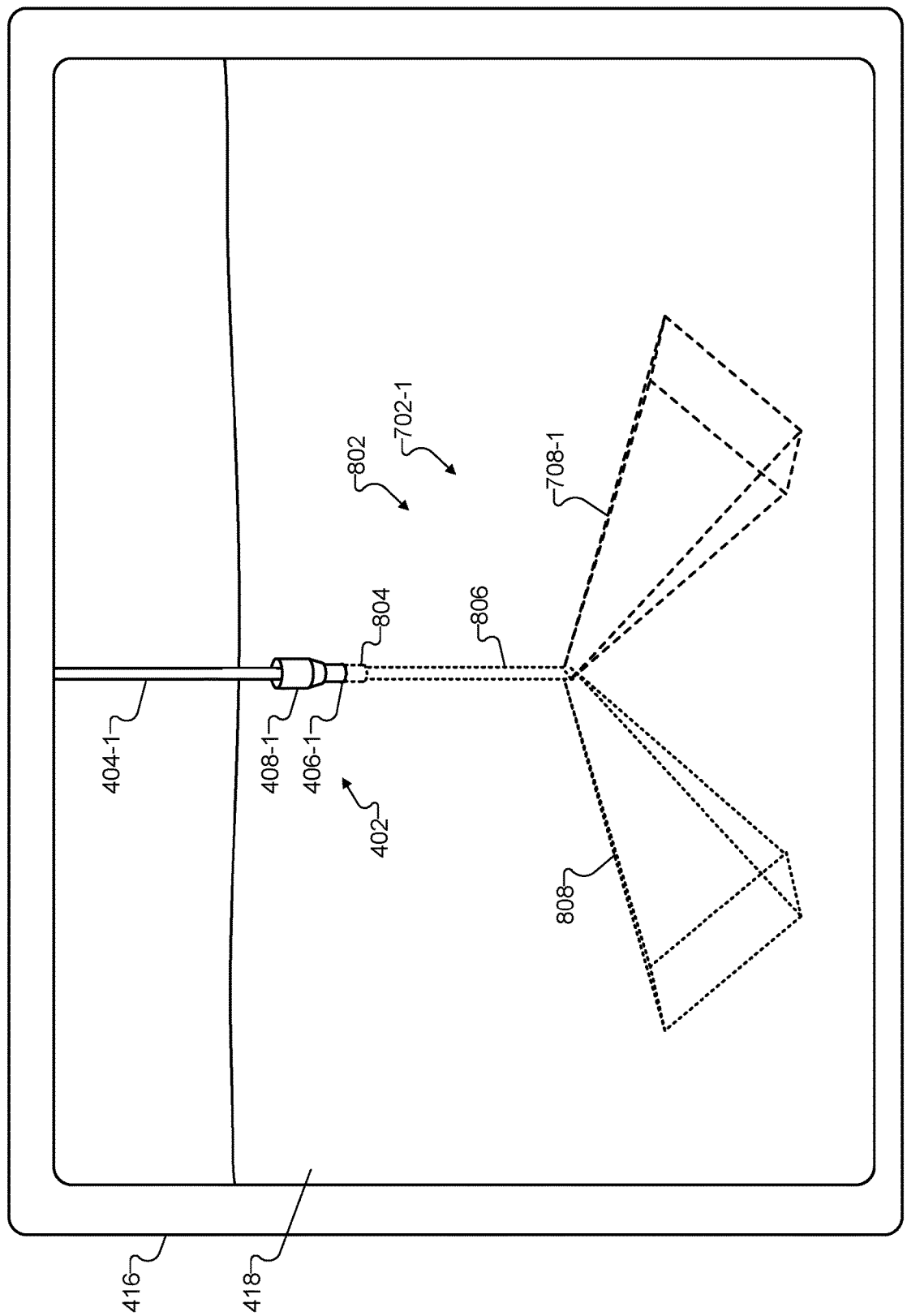
Figure 9:
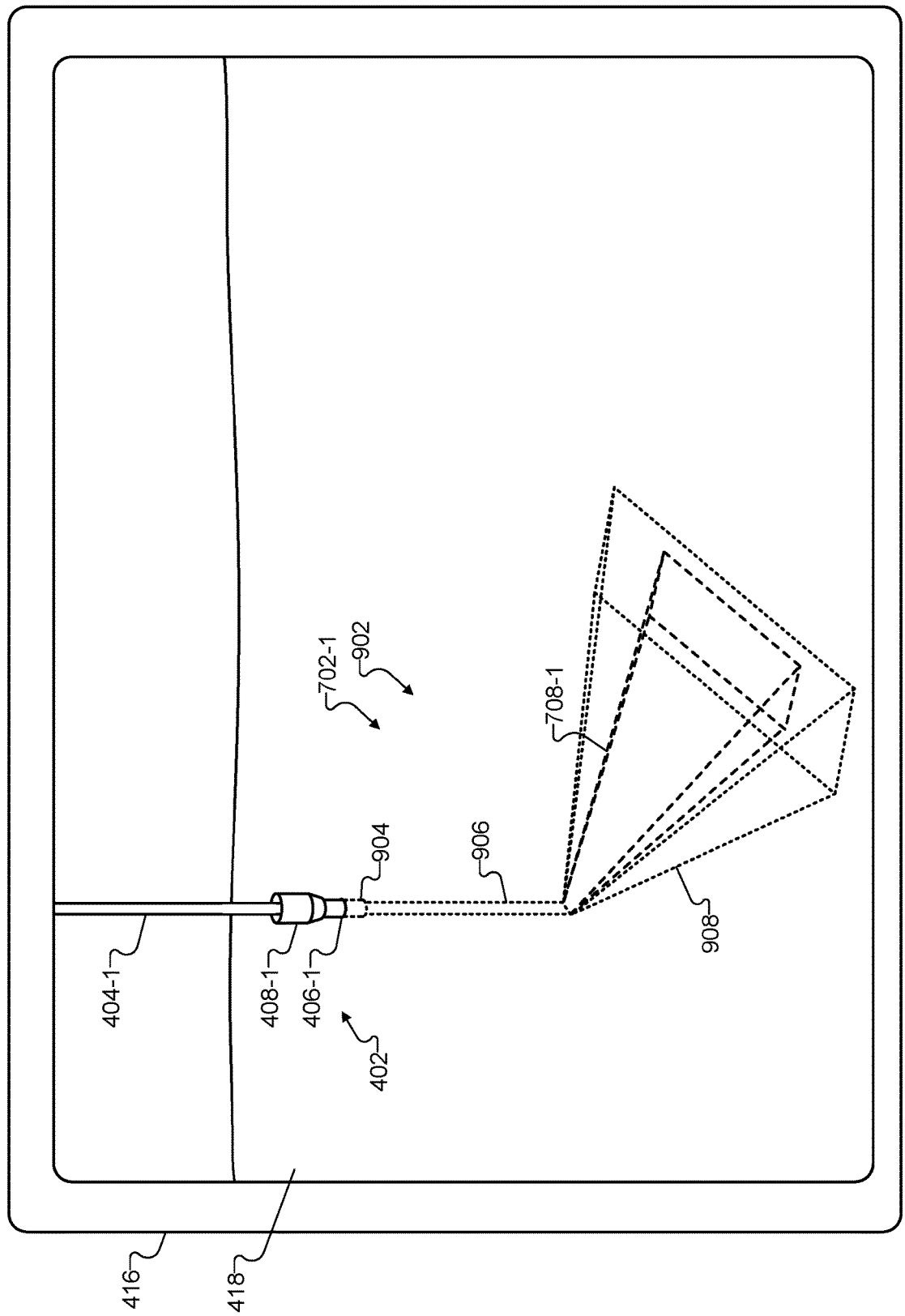
Figure 10:
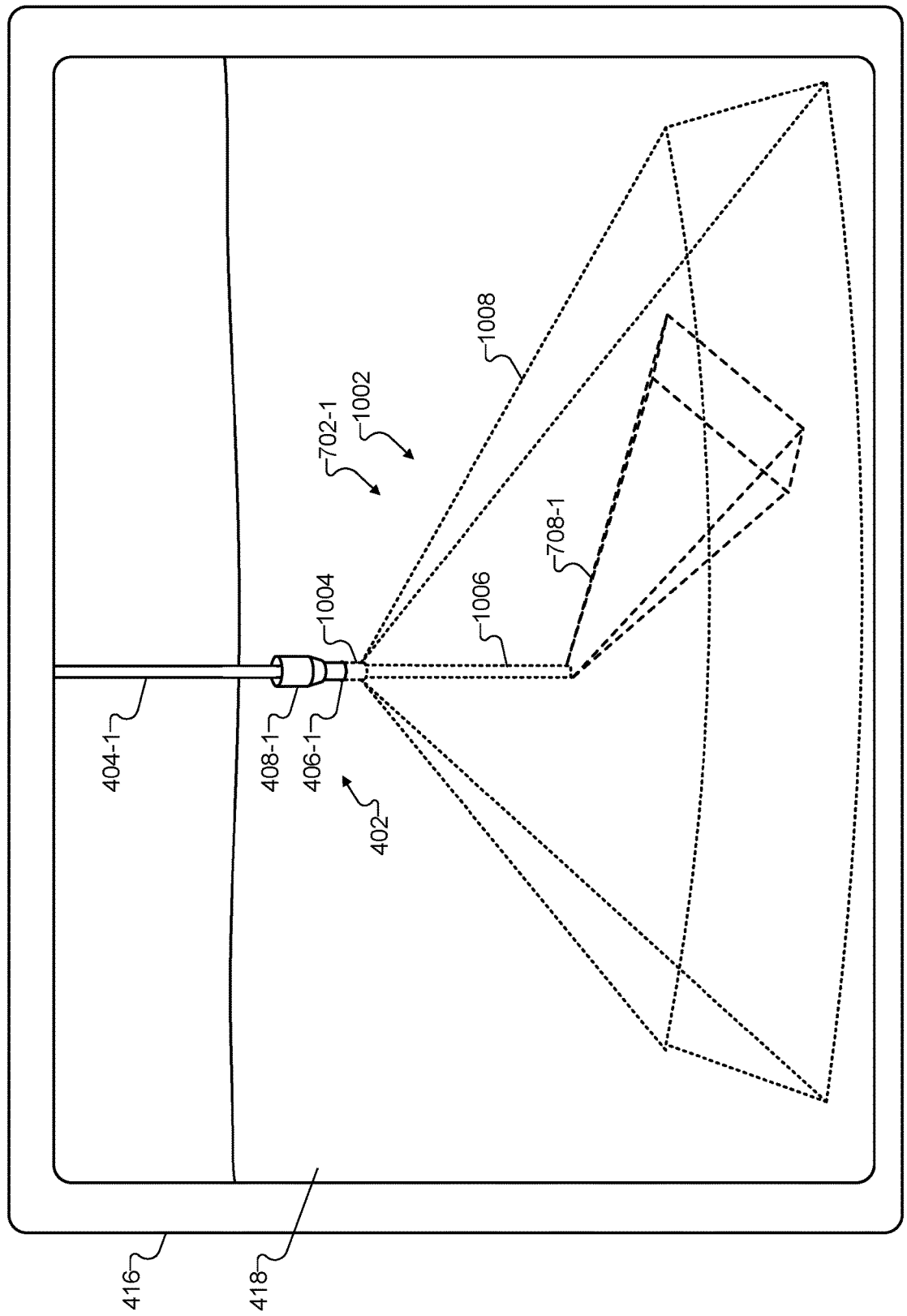

As further shown in each of FIGS. 7-10, mixed reality presentation 418 includes, along with the real elements of external view 402, different shape overlays each including one or more virtual elements. Specifically, each of FIGS. 7-10 depict a standard shape overlay 702-1 indicative of the extent of the current field of view of active imaging device 404-1 together with a different auxiliary shape overlay indicative of the extent of a potential field of view. For example, FIG. 7 shows an auxiliary shape overlay 702-2, FIG. 8 shows an auxiliary shape overlay 802, FIG. 9 shows an auxiliary shape overlay 902, and FIG. 10 shows an auxiliary shape overlay 1002.

Each of these standard and auxiliary shape overlays will be described in more detail below and will be understood to be different exemplary implementations of shape overlay 420, described above. As depicted in FIGS. 7-10, each of the virtual elements of the respective shape overlays are drawn with dashed or dotted lines. Specifically, the depiction of standard shape overlay 702-1 in each figure is drawn using dashed lines, while the depiction of the respective auxiliary shape overlay, as well as elements that may be part of either or both shape overlays, are drawn using dotted lines. As mentioned above and as shown, the virtual elements of the shape overlays are displayed on display device 416 so as to be integrated with external view 402 (i.e., so as to overlap and integrate with the real elements of external view 402).

FIG. 7 shows standard shape overlay 702-1 and auxiliary shape overlay 702-2, each of which depict a virtual portion 704 of cannula 408-1 and a virtual portion 706 of active imaging device 404-1. Shape overlays 702-1 and 702-2 depict different respective shapes 708 (i.e., shape 708-1 for standard shape overlay 702-1, and shape 708-2 for auxiliary shape overlay 702-2) that indicate the extent of the current and potential fields of view, respectively.

Virtual portions 704 and 706 may represent portions of cannula 408-1 and active imaging device 404-1, respectively, that are not visible in external view 402. For example, the represented portions of cannula 408-1 and active imaging device 404-1 may not be visible due to having been inserted into the body at port 406-1 so as to be located beneath the external surface of the body (e.g., the skin). As mentioned above, unlike shapes 708, virtual portions 704 and 706 may be identical for both shape overlays 702-1 and 702-2. As such, it will be understood that these virtual objects may be displayed as part of either or both of shape overlays 702-1 and 702-2.

Shapes 708-1 and 708-2 may represent different fields of view and, as such, may be displayed concurrently or one at a time. For instance, in certain examples, system 100 may direct display device 416 to display auxiliary shape overlay 702-2 (including shape 708-2) by itself, while abstaining from displaying shape overlay 702-1 (including shape 708-1). Conversely, in other examples, system 100 may direct display device 416 to display auxiliary shape overlay 702-2 (including shape 708-2) concurrently with displaying shape overlay 702-1 (including shape 708-1), as shown in FIG. 7. In these examples, shape overlays 702-1 and 702-2 may be rendered so as to be visually distinguishable in various ways including, but not limited to, rendering the shape overlays with different colors, line styles, transparencies, shadings, textual or graphical annotations, animations (e.g., blinking shapes, etc.), or the like. Alternatively, shape overlays 702-1 and 702-2 may be presented using like colors and styles, etc., such that the shape overlays are not explicitly rendered to be visually distinguishable.

In some examples, the concurrency of displaying both shape overlays 702-1 and 702-2 may be transitory. For example, while standard shape overlay 702-1 is indicative of the current field of view of active imaging device 404-1, auxiliary shape overlay 702-2 may be indicative of a potential field of view corresponding to a previous position at which active imaging device 404-1 was located prior to the displaying of auxiliary shape overlay 702-2. For instance, auxiliary shape overlay 702-2 may be a transitory "trail" to help emphasize movement of the current field of view from one pose to another (e.g., analogous to a cursor trail used to increase visibility of a mouse cursor in a conventional computer operating system).

In other examples, the concurrency of displaying both shape overlays 702-1 and 702-2 may be more enduring and less transitory. For example, in an implementation in which active imaging device 404-1 is configured to capture imagery of the internal view stereoscopically from a pair of stereoscopic image sensors included within active imaging device 404-1, the current field of view indicated by standard shape overlay 702-1 may correspond to a first image sensor in the pair of stereoscopic image sensors while the potential field of view indicated by auxiliary shape overlay 702-2 corresponds to a second image sensor in the pair of stereoscopic image sensors. In one example, for instance, shape 708-1 may indicate a left-side field of view of active imaging device 404-1 while shape 708-2 indicates a right-side field of view of the active imaging device 404-2.

As another example of an auxiliary shape overlay, certain implementations of active imaging device 404-1 may be configured to capture the imagery of the internal view from different viewing angles relative to active imaging device 404-1 by employing at least one of an angled lens and a distal articulation mechanism. In this example, the current field of view indicated by standard shape overlay 702-1 may correspond to a first viewing angle from which active imaging device 404-1 is capturing the imagery, while the potential field of view indicated by auxiliary shape overlay 702-2 corresponds to a second viewing angle from which active imaging device 404-1 is configured to capture the imagery. The second viewing angle may be distinct from the first viewing angle. For example, as shown in FIG. 7, the second viewing angle associated with shape 708-2 may correspond to a different articulation of the articulation mechanism than the first viewing angle associated with shape 708-1.

As yet another example of an auxiliary shape overlay that system 100 may cause to be enabled, FIG. 8 illustrates, along with standard shape overlay 702-1, an auxiliary shape overlay 802. Auxiliary shape overlay 802 depicts virtual portions 804 and 806 that (like virtual portions 704 and 706) represent occluded portions of cannula 408-1 and active imaging device 404-1. Auxiliary shape overlay 802 further depicts shape 808. In FIG. 8, shape 708-1 may indicate a current field of view for a manner in which active imaging device 404-1 is currently angled, oriented, articulated, or the like. Shape 808 may indicate a potential field of view indicative of a potential field of view for a second manner in which active imaging device 404-1 may potentially be angled, oriented, and/or articulated (e.g., after a setting is changed on active imaging device 404-1, after active imaging device 404-1 is moved or reoriented, etc.). For example, shape 808 may indicate a field of view for active imaging device 404-1 if a setting of the active imaging device is changed from a positive to a negative viewing angle (e.g., 30° up to 30° down) or vice versa.

As yet another example, FIG. 9 illustrates, along with standard shape overlay 702-1, an auxiliary shape overlay 902. Auxiliary shape overlay 902 depicts virtual portions 904 and 906 that (like virtual portions 704 and 706) represent occluded portions of cannula 408-1 and active imaging device 404-1. Auxiliary shape overlay 902 further depicts shape 908, which may be indicative of various different potential fields of view.

For instance, in one implementation, active imaging device 404-1 may be configured to provide the captured imagery at different zoom levels. The current field of view indicated by standard shape overlay 702-1 may thus correspond to a first zoom level at which active imaging device 404-1 is providing the captured imagery, while the potential field of view indicated by auxiliary shape overlay 902 corresponds to a second zoom level at which active imaging device 404-1 is configured to provide the captured imagery. The second zoom level may be distinct from the first zoom level. For example, as shown in FIG. 9, the second zoom level associated with shape 908 may correspond to a different zoom level (e.g., a wider zoom level) than the first zoom level associated with shape 708-1. In other examples (not explicitly shown by FIG. 9), the zoom level associated with shape 908 may instead correspond to a zoom level that is tighter (rather than wider) than the zoom level associated with shape 708-1. The zoom levels described herein and illustrated by FIG. 9 will be understood to refer to any suitable types of zoom levels associated with any type of zoom technology such as a digital zoom, an optical zoom, or the like.

Still referring to FIG. 9, in the same or another implementation, active imaging device 404-1 may be configured to provide the captured imagery of the internal view by way of one imaging technology at a time from a plurality of imaging technologies supported by active imaging device 404-1. The current field of view indicated by standard shape overlay 702-1 may thus correspond to a first imaging technology in the plurality of imaging technologies, while the potential field of view indicated by auxiliary shape overlay 902 corresponds to a second imaging technology in the plurality of imaging technologies. The second imaging technology may be distinct from the first imaging technology. For example, as shown in FIG. 9, the second imaging technology associated with shape 908 may correspond to a different imaging technology (e.g., an ultrasound imaging technology, a hyperspectral imaging technology, a fluorescence-based imaging technology, a motion-amplification imaging technology, etc.) than the first imaging technology associated with shape 708-1 (e.g., a standard visible-light-based imaging technology).

As yet another example, FIG. 10 illustrates, along with standard shape overlay 702-1, an auxiliary shape overlay 1002. As with other auxiliary shape overlays described above, auxiliary shape overlay 1002 is shown to depict virtual portions 1004 and 1006 that (like virtual portions 704 and 706) represent occluded portions of cannula 408-1 and active imaging device 404-1. While shape overlay 1002 may display these elements in certain implementations (e.g., to illustrate the current position of the occluded portion of active imaging device 404-1 even while illustrating a field of view originating from a different position), these elements may, in other implementations, be displayed only by standard shape overlay 702-1. Auxiliary shape overlay 1002 further depicts a shape 1008, which may be indicative of various different potential fields of view.

For instance, in one implementation, shape 1008 may be indicative of a potential field of view having the widest possible zoom level for the position of port 406-1 and cannula 408-1 in the body. Specifically, as shown, rather than originating from the distal end of active imaging device 404-1 as in FIG. 7-9, shape 1008 originates from a mouth of cannula 408-1 to show, in one example, the widest zoom angle that may be possibly captured by active imaging device 404-1 from within cannula 408-1 at port 406-1. In other examples (not explicitly shown in FIG. 10), shape 1008 could instead be depicted to illustrate the tightest zoom angle that may be possible from cannula 408-1 (e.g., based on the length of active imaging device 404-1 and/or the extent to which active imaging device 404-1 is configured to be inserted into the body). Still referring to FIG. 10, in another implementation, shape 1008 may be indicative of a potential field of view associated with a panorama-type mosaic of all the internal portions of the body that have been imaged as active imaging device 404-1 has moved about within the body, a potential field of view associated with stitched imagery from a plurality of different imaging devices that may be in use concurrently, or the like.

In the examples of auxiliary shape overlays described above, auxiliary shape overlays have been described that enhance a user's understanding of the current field of view of the active imaging device by allowing a standard shape overlay representative of the current field of view to easily be contrasted with an auxiliary shape overlay representative of a field of view at a previous position of the active imaging device, or a potential field of view that is achievable by the active imaging device or another imaging device that could be used in its place.

In the following examples, yet another purpose of displaying an auxiliary shape overlay will be described. Specifically, an auxiliary shape overlay may be used to facilitate the swapping of an active imaging device for a different imaging device (e.g., using the same or a different port and/or manipulator arm), for moving the active imaging device to a different port or manipulator arm, or for other such changes. For instance, the auxiliary shape overlay may be frozen in place temporarily to act as a placeholder to facilitate a user in aligning a new standard shape overlay (e.g., associated with a replacement imaging device, a same imaging device at a new port, etc.) with the pose of the old shape overlay. In this way, the operation may be performed with minimal interruption when the change is implemented to swap in the replacement imaging device, change to the new port, or the like.

In one example scenario of this type, system 100 may identify an operating condition associated with the operation performed on the body by detecting, during the performance of the operation, an initiation of a process to swap out the active imaging device for an additional imaging device. For example, a team member 210 (e.g., clinician 210-1) performing the operation may determine that it would be desirable to swap out the active imaging device for an additional imaging device that employs a different imaging technology, supports different settings (e.g., zoom level settings, articulation or viewing angle settings, etc.), or the like. As such, system 100 may direct the display device to toggle the display of the shape overlay indicative of the current field of view to begin to display the shape overlay at a static position with respect to the body. Subsequent to beginning to display the shape overlay at the static position, system 100 may determine that the display device is to further display an additional shape overlay together with the shape overlay and the external view of the body. For example, the additional shape overlay may be indicative of an extent (relative to the body) of an additional field of view corresponding to the additional imaging device as the process to swap out the active imaging device for the additional imaging device is performed. Based on the determining that the display device is to display the additional shape overlay, system 100 may direct the display device to display the additional shape overlay together with the shape overlay and the external view of the body. System 100 may then direct the display device to persist in displaying the shape overlay at the static position at least until the additional shape overlay overlaps with the shape overlay at the static position (e.g., until the additional shape overlay is at least approximately aligned with where the shape overlay was positioned when the process to swap out the active imaging device was initiated).

In another example scenario of this type, system 100 may identify an operating condition associated with the operation performed on the body by detecting, during the performance of the operation, an initiation of a process to move the active imaging device from a first port into the body by way of which the active imaging device captures the imagery of the internal view to a second port into the body. For example, a team member 210 performing the operation (e.g., whether using a manual active imaging device or a computer-controlled active imaging device attached to a manipulator arm) may determine that the active imaging device could more conveniently provide more beneficial imagery of the internal view from a perspective provided by a different port, that it would be beneficial for another instrument to use the first port instead of the active imaging device, or that the operation would otherwise benefit from moving the active imaging device to the second port for any other suitable reason. As such, system 100 may direct the display device to toggle the display of the shape overlay indicative of the current field of view to begin to display the shape overlay at a static position with respect to the body. Subsequent to beginning to display the shape overlay at the static position, system 100 may determine that the display device is to further display an additional shape overlay together with the shape overlay and the external view of the body. For example, the additional shape overlay may be indicative of an extent (relative to the body) of an additional field of view corresponding to the field of view of the active imaging device as the process to move the active imaging device is performed. Based on the determining that the display device is to display the additional shape overlay, system 100 may direct the display device to display the additional shape overlay together with the shape overlay and the external view of the body. System 100 may then direct the display device to persist in displaying the shape overlay at the static position at least until the additional shape overlay overlaps with the shape overlay at the static position (e.g., until the additional shape overlay is at least approximately aligned with where the shape overlay was positioned when the process to move the active imaging device was initiated).

In yet another example scenario of this type, system 100 may identify an operating condition associated with the operation performed on the body by detecting, during the performance of the operation, an initiation of a process to move the active imaging device from being attached to a first manipulator arm to being attached to a second manipulator arm. For example, the move from the first to the second manipulator arm may be associated with a move from one port to another or may be performed for other reasons (e.g., to leverage different capabilities and/or positioning of different manipulator arms, etc.). As such, system 100 may direct the display device to toggle the display of the shape overlay indicative of the current field of view to begin to display the shape overlay at a static position with respect to the body. Subsequent to beginning to display the shape overlay at the static position, system 100 may determine that the display device is to further display an additional shape overlay together with the shape overlay and the external view of the body. For example, the additional shape overlay may be indicative of an extent (relative to the body) of an additional field of view corresponding to the field of view of the active imaging device as the process to move the active imaging device is performed. Based on the determining that the display device is to display the additional shape overlay, system 100 may direct the display device to display the additional shape overlay together with the shape overlay and the external view of the body. System 100 may then direct the display device to persist in displaying the shape overlay at the static position at least until the additional shape overlay overlaps with the shape overlay at the static position (e.g., until the additional shape overlay is at least approximately aligned with where the shape overlay was positioned when the process to move the active imaging device was initiated).

To illustrate how system 100 may facilitate any such process for moving and/or swapping out an imaging device during an operation as described in any of these or other similar examples, FIGS. 11A-11D illustrate display device 416 displaying different exemplary shape overlays. Specifically, FIGS. 11A-11D illustrate a sequence of snapshots of mixed reality presentation 418 as the process for moving and/or swapping out the imaging device during the operation is performed. Across different snapshots depicted in FIGS. 11A-11D, different shape overlays are used to represent the field of view of active imaging device 404-1 when active imaging device 404-1 is at different positions relative to the body. In FIGS. 11A-11D, these different shape overlays depict the field of view as having different angles with respect to the same shaft of imaging device 404-1 when active imaging device 404-1 is at different positions relative to the body. It will be understood that this change in field of view angle relative to the body may exist because of articulation of an articulating mechanism (e.g., bending of an articulating wrist), bending of the shaft, redirecting of the optics of active imaging device 404-1, or because of other such features that may be included in active imaging device 404-1 but are not explicitly illustrated in FIGS. 11A-D. It will also be understood that certain imaging devices that lack such features may not articulate their field of view in this way; such an imaging device, for instance, would have a field of view characterized by a consistent angle with respect to the shaft and roll of the shaft of the imaging device.

Figure 11A:
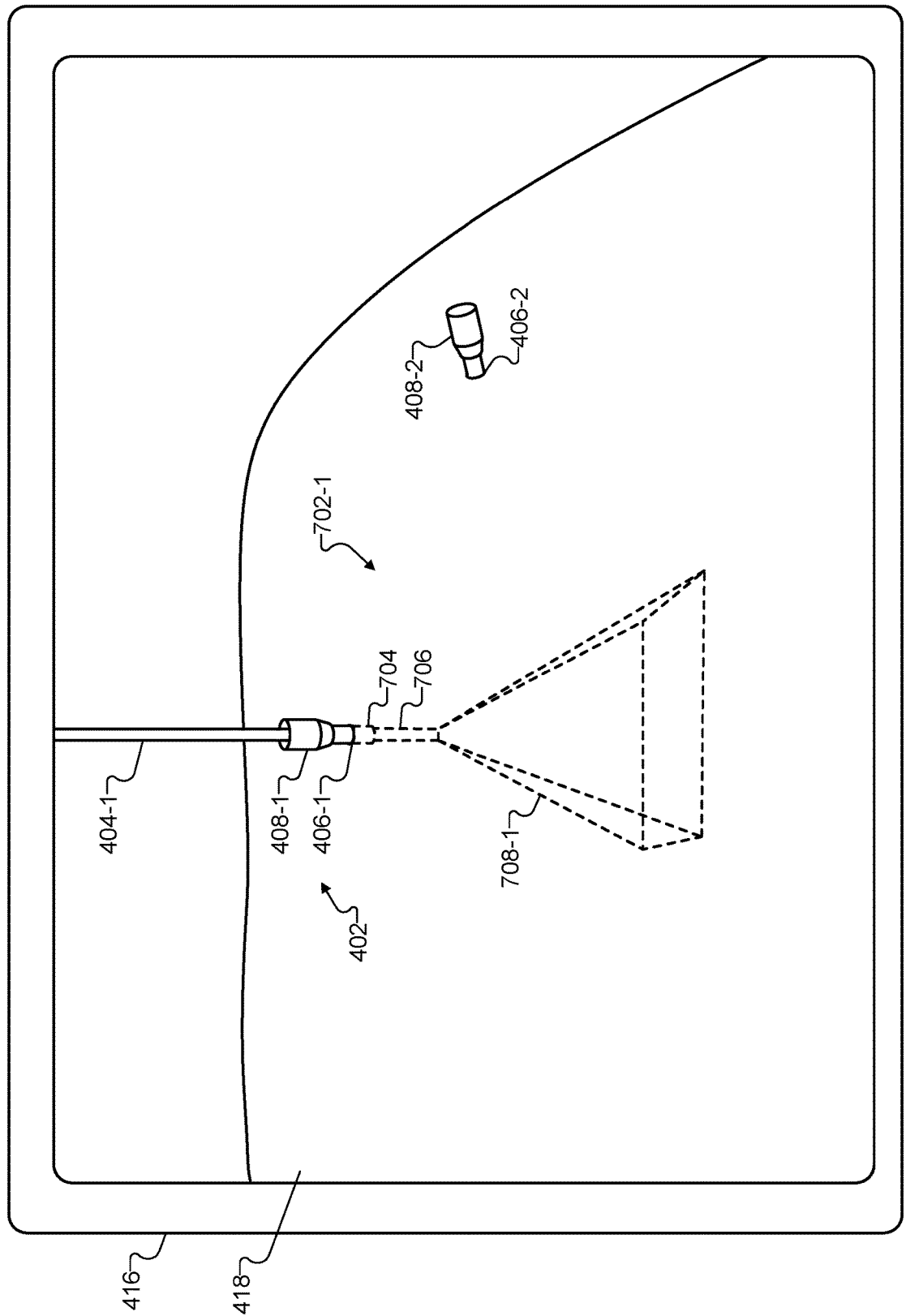

Referring first to FIG. 11A, as with FIGS. 7-10 above, FIG. 11A illustrates external view 402 of the body upon which the operation is being performed, along with such real-world elements as active imaging device 404-1, which is inserted into the body at port 406-1 by way of cannula 408-1, and cannula 408-2 at port 406-2. Along with the real-world elements shown in external view 402, FIG. 11A further shows standard shape overlay 702-1, which depicts virtual portion 704 to represent an occluded portion of cannula 408-1 and virtual portion 706 to represent an occluded portion active imaging device 404-1. Additionally, shape overlay 702-1 further depicts shape 708-1 indicative of the current field of view of active imaging device 404-1 as the operation is ongoing.

At the moment illustrated in FIG. 11A, system 100 detects an initiation of a process to swap out or move active imaging device 404-1 in at least one of the ways described in the examples above or in another suitable manner. For instance, at this moment, system 100 may detect the initiation of a process to swap out active imaging device 404-1 for an additional imaging device, a process to move the active imaging device from port 406-1 to port 406-2, a process to move active imaging device 404-1 from being attached to a first manipulator arm (not explicitly shown) to being attached to a second manipulator arm (also not shown), or the like. For purposes of the present example, it will be assumed that system 100 detects an initiation of a process to implement all three of these exemplary changes (i.e., to swap out active imaging device 404-1 while also moving to port 406-2 and to a different manipulator arm). However, it will be understood that only one or two of these changes may be implemented in other examples.

Once system 100 detects the initiation of the process to swap out and/or change active imaging device 404-1 (e.g., based on input received from a user, from a medical system of which active imaging device 404-1 is a part, etc.), system 100 may direct display device 416 to begin displaying shape overlay 702-1 at a static position with respect to the body. For example, system 100 may direct display device 416 to freeze the display of shape overlay 702-1 (or at least portions thereof such as shape 708-1) in place where they are so as to act as a placeholder while the process to move and/or swap out active imaging device 404-1 is performed. When any process for moving and/or swapping out an imaging device are performed, an ongoing operation may be disrupted to some extent while the process to move or swap out the imaging device is performed. However, this disruption may be minimized if the changed imaging device (e.g., the replacement imaging device, the same imaging device in the new port, etc.) can be quickly and conveniently brought back to at least approximate alignment with where the previous imaging device (e.g., the original imaging device, the imaging device in the previous port) had been prior to the initiation of the process. In this way, it may be easy for those performing the operation (e.g., clinician 210-1) to become oriented to the changed imaging device.

In some examples, data such as stored kinematic data may be employed to automatically facilitate the system in achieving such alignment of the changed imaging device to the previous imaging device. However, in other examples, such data may not be available. For example, the changed active imaging device may be a manual imaging device for which no kinematic data is stored, or may be a computer controlled imaging device on a manipulator arm associated with a distinct manipulating system that has no known spatial relationship to the manipulating system of the original manipulator arm. In either case, it may be useful for system 100 to display shape overlay 702-1 at the static position and to persist in doing so at least until a new shape overlay approximately aligns with (e.g., overlaps with) shape overlay 702-1. It may be particularly useful, however, in those examples in which other ways of achieving the alignment are not available.

FIG. 11B shows that shape 708-1 of shape overlay 702-1 persists (i.e., continues to be displayed by display device 416 under direction from system 100) even after active imaging device 404-1 has been removed. In some examples, portions 704 and/or 706 may be depicted in the persistent shape overlay 702-1 as well, although FIG. 11B shows only that shape 708-1 persists in this way.

Figure 11C:
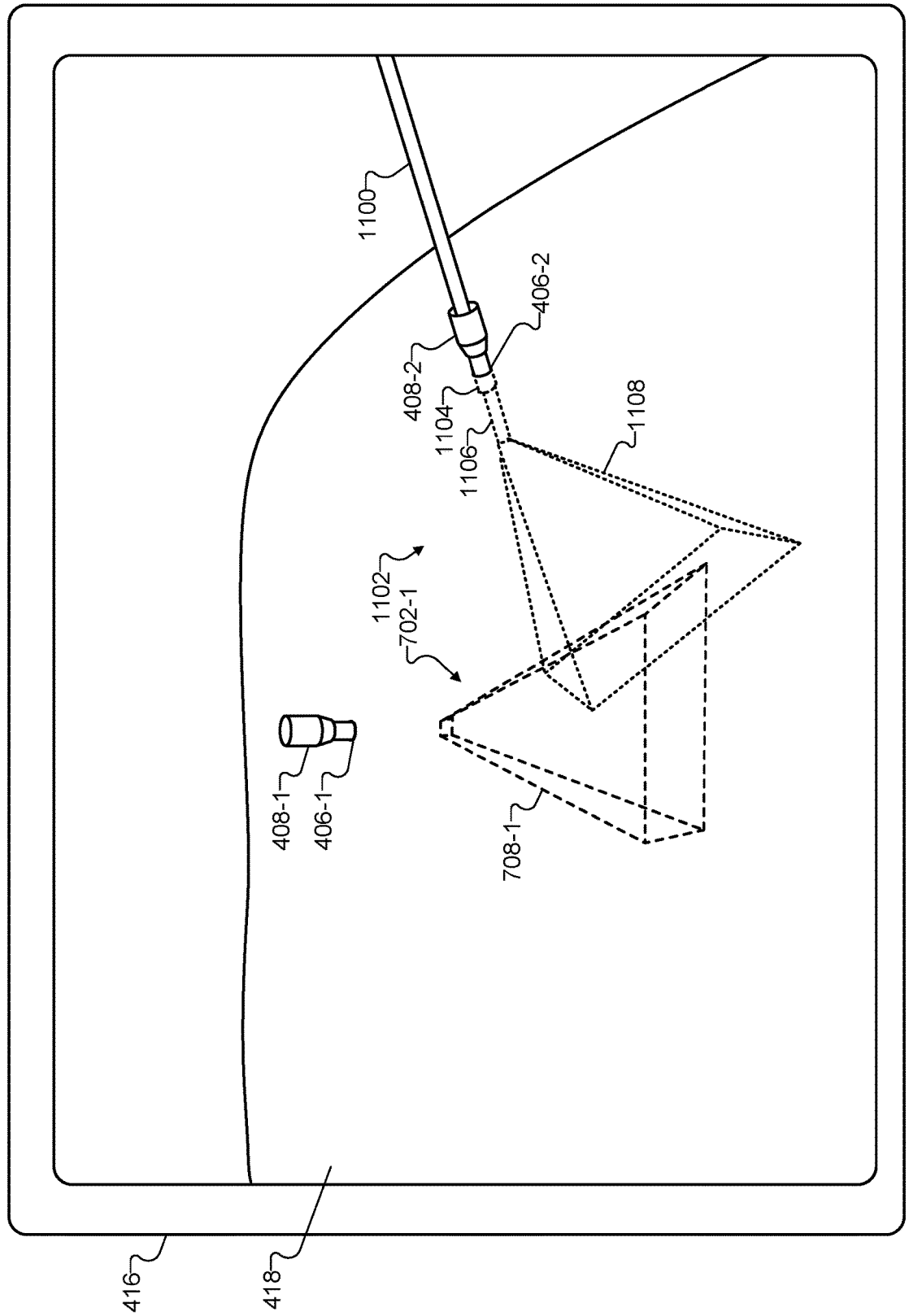

FIG. 11C shows a replacement active imaging device 1100 (also referred to as an "additional" or "changed" imaging device) being inserted by way of cannula 408-2 at port 406-2. While, in this example, active imaging device 1100 is a different imaging device from imaging device 404-1 (which was removed), it will be understood that, in certain other examples, active imaging device 1100 may be the same as imaging device 404-1 (i.e., active imaging device 404-1 may simply be moved from port 406-1 to 406-2).

As shown, the depiction of shape 708-1 in shape overlay 702-1 may persist within mixed reality presentation 418 while active imaging device 1100 is being inserted and moved around within the body in an attempt to achieve alignment of the field of view of active imaging device 1100 with the previous field of view of imaging device 404-1 (when imaging device 404-1 was active). Additionally, a shape overlay 1102 that includes a virtual portion 1104 of cannula 408-2, a virtual portion 1106 of active imaging device 1100, and a shape 1108 representative of the extent of the current field of view of active imaging device 1100 is also shown in mixed reality presentation 418. Thus, for example, a user being presented with mixed reality presentation 418 on display device 416 may see both shape overlays 702-1 and 1102, and may attempt to achieve at least an approximate alignment of shape overlay 1102 with shape overlay 702-1 (which is frozen in place at the static position).

Figure 11D:
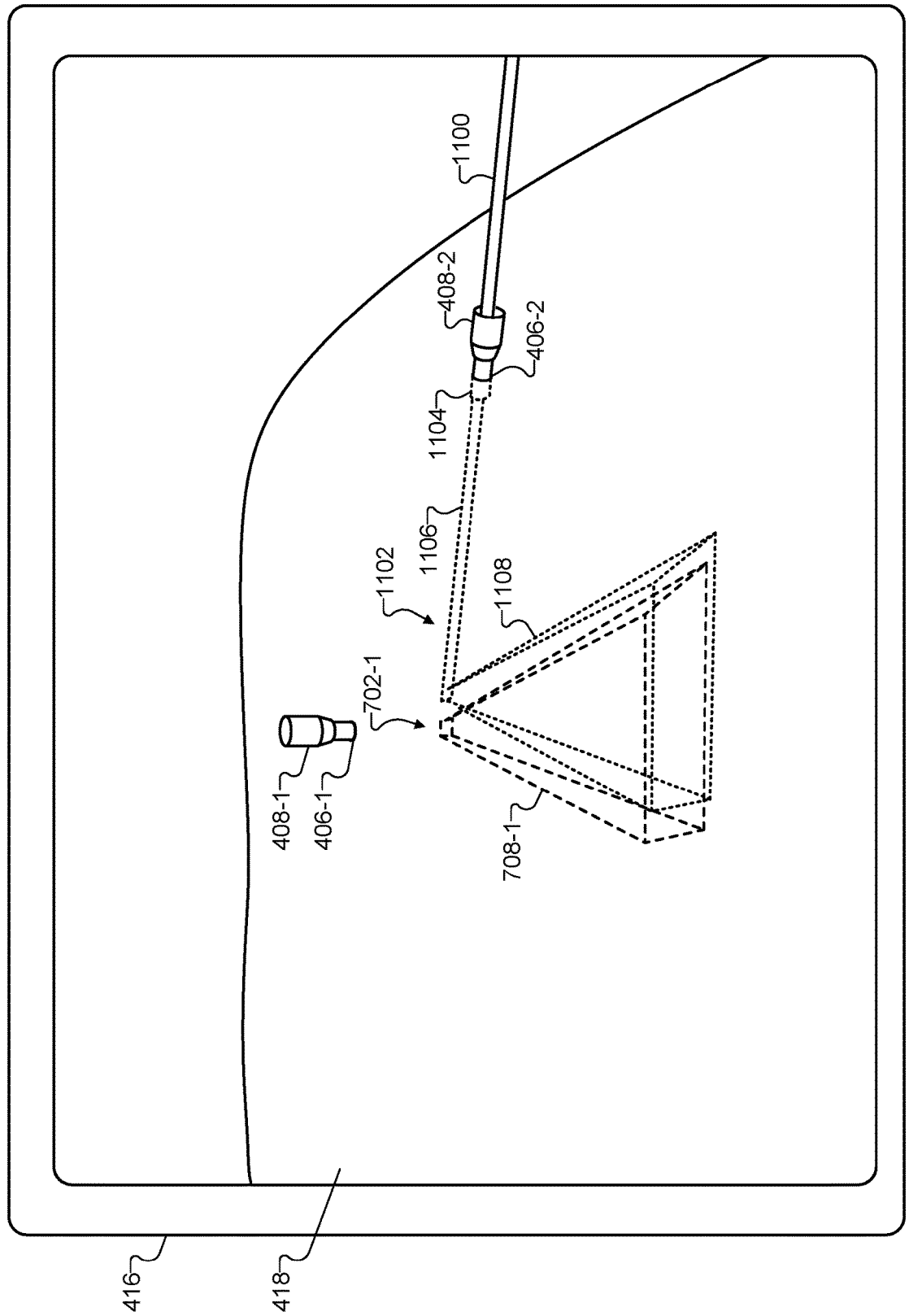

FIG. 11D illustrates the view when such approximate alignment has been achieved. Specifically, as shown, shape overlay 1102 (and shape 1108 in particular) is shown to be overlapping with shape 708-1 in shape overlay 702-1. As used herein, two shape overlays may be determined to be at least approximately aligned when, like shape overlays 702-1 and 1102 in FIG. 11D, the shape overlays are overlapping and are oriented in approximately the same direction (e.g., both generally pointing down in this example). Once system 100 determines that the approximate alignment of the two shape overlays has thus been achieved, it may no longer be necessary or useful for display device 416 to persist is displaying the previous shape overlay (e.g., shape overlay 702-1) at the static position. As such, when alignment has thus been detected, system 100 may direct display device 416 to toggle off (i.e., cease displaying) the display of shape overlay 702-1, while continuing to display shape overlay 1102 of the replacement active imaging device 1100.

Figure 12:
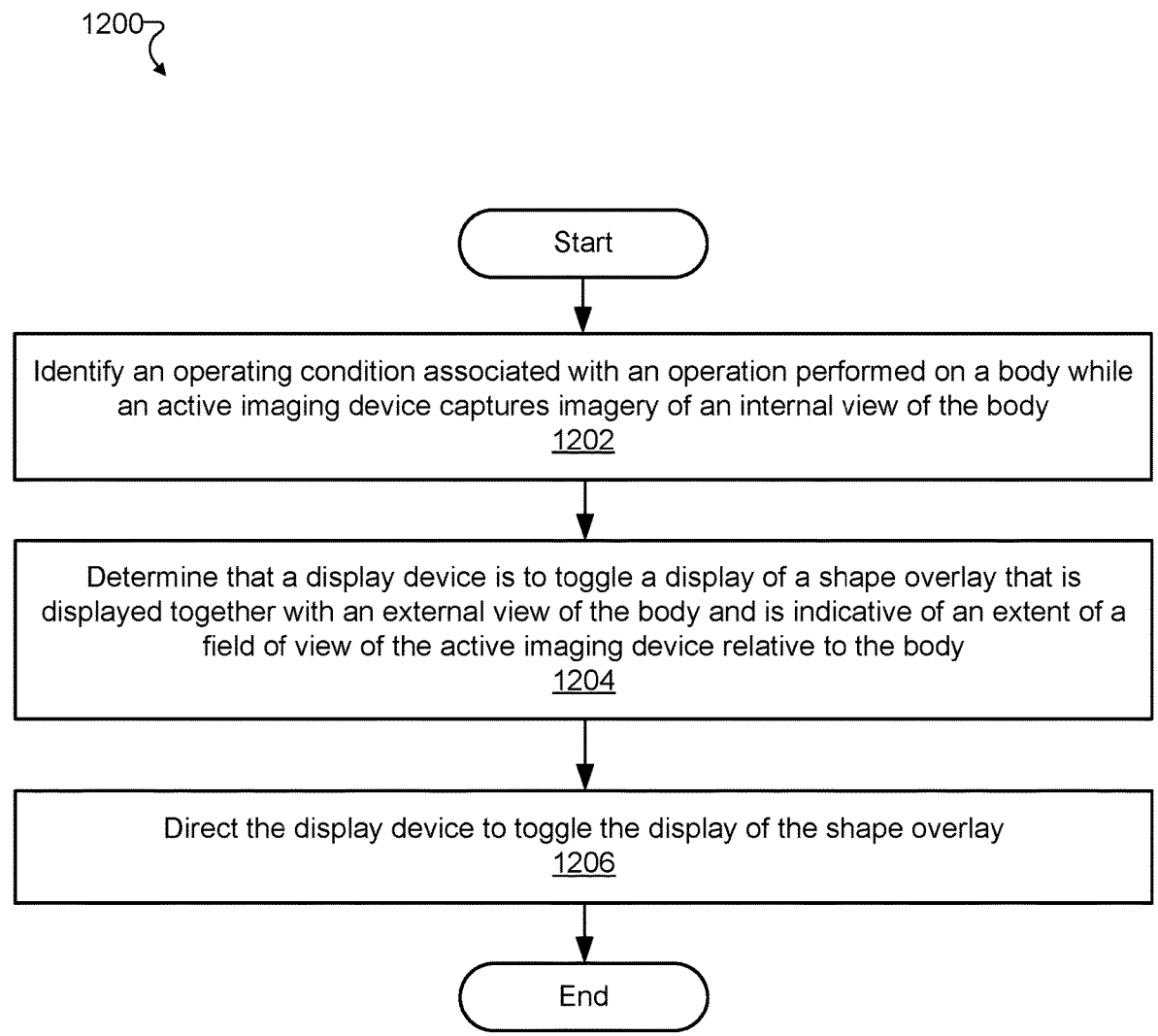
FIG. 12 illustrates an exemplary mixed reality method for indicating an extent of a field of view of an imaging device according to principles described herein.

FIG. 12 illustrates an exemplary method 1200 for indicating an extent of a field of view of an imaging device. While FIG. 12 illustrates exemplary operations according to one embodiment, other embodiments may omit, add to, reorder, and/or modify any of the operations shown in FIG. 12. One or more of the operations shown in FIG. 12 may be performed by a mixed reality presentation system such as system 100, any components included therein, and/or any implementation thereof.

In operation 1202, a mixed reality presentation system may identify an operating condition associated with an operation performed on a body while an active imaging device captures imagery of an internal view of the body. Operation 1202 may be performed in any of the ways described herein.

In operation 1204, the mixed reality presentation system may determine that a display device is to toggle a display of a shape overlay. For example, the shape overlay may be displayed together with an external view of the body, and may be indicative of an extent of a field of view of the active imaging device relative to the body. In some examples, operation 1204 may be performed based on the operating condition identified in operation 1202. Operation 1204 may be performed in any of the ways described herein.

In operation 1206, the mixed reality presentation system may direct the display device to toggle the display of the shape overlay. For example, the mixed reality presentation system may direct the display device to toggle the display of the shape overlay based on the determining in operation 1204 that the display device is to toggle the display of the shape overlay. Operation 1206 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

In some examples, any of the systems and/or other components described herein may be implemented by a computing device including one or more processors, storage devices, input/output modules, communication interfaces, buses, infrastructures, and so forth. For instance, storage facility 102 of system 100 may be implemented by a storage device of the computing device, and processing facility 104 of system 100 may be implemented by one or more processors of the computing device. In other examples, the systems and/or other components described herein may be implemented by any suitable non-transitory computer-readable medium storing instructions that, when executed, direct a processor of such a computing device to perform methods and operations described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A computer-assisted medical system comprising:
   a manipulator arm coupled to an active imaging device; and
   one or more processors configured to:
   identify an operating condition associated with an operation performed on a body while the active imaging device captures imagery of an internal view of the body,
   determine, based on the identified operating condition, that a display device is to toggle a display of a shape overlay from a first state to a second state while an external view of the body as captured by an external image capture device positioned external to the body is being displayed by the display device, the shape overlay indicative of an extent of a field of view of the active imaging device relative to the body, and based on the determining that the display device is to toggle the display of the shape overlay from the first state to the second state, direct the display device to toggle the display of the shape overlay from the first state to the second state, the directing the display device to toggle the display of the shape overlay from the first state to the second state comprising:

directing, when the shape overlay is not being displayed when the operating condition is identified, the display device to begin displaying the shape overlay together with the external view of the body as captured by the external image capture device, and directing, when the shape overlay is being displayed when the operating condition is identified, the display device to cease displaying the shape overlay together with the external view of the body as captured by the external image capture device.

2. The computer-assisted medical system of claim 1, wherein the identifying of the operating condition comprises detecting a position of a distal end of the active imaging device in relation to an internal area of the body from which the active imaging device captures the imagery of the internal view.

3. The computer-assisted medical system of claim 1, wherein the identifying of the operating condition comprises detecting an operational status of at least one of:

an image sensor included in the active imaging device, a communication link by way of which the active imaging device provides data associated with the imagery, and a light source associated with the active imaging device and configured to illuminate an internal area of the body from which the active imaging device captures the imagery.

4. The computer-assisted medical system of claim 1, wherein the identifying of the operating condition comprises determining a status of an object insertion process in which an object is inserted into an internal area of the body.

5. The computer-assisted medical system of claim 4, wherein:

the shape overlay is being displayed when the operating condition is identified;

the determining of the status of the object insertion process comprises detecting that the object is visible within the field of view; and the directing of the display device to toggle the display comprises directing the display device to cease displaying the shape overlay based on the detection that the object is visible within the field of view.

6. The computer-assisted medical system of claim 1, wherein the one or more processors are further configured to direct the display device to display, together with the external view of the body and the shape overlay, a simulated depiction of an internal portion of the body, the simulated depiction displayed so as to appear to be behind the shape overlay.

7. The computer-assisted medical system of claim 1, wherein the one or more processors are further configured to:

determine that the display device is to display an auxiliary shape overlay together with the external view of the body, the auxiliary shape overlay indicative of an extent, relative to the body, of a potential field of view of an auxiliary imaging device that is distinct from the active imaging device; and based on the determining that the display device is to display the auxiliary shape overlay, direct the display device to display the auxiliary shape overlay together with the external view of the body.

8. The computer-assisted medical system of claim 1, wherein the one or more processors are further configured to:

determine that the display device is to display an auxiliary shape overlay together with the external view of the body, the auxiliary shape overlay indicative of an extent, relative to the body, of a potential field of view of the active imaging device, the potential field of view distinct from the field of view; and based on the determining that the display device is to display the auxiliary shape overlay, direct the display device to display the auxiliary shape overlay together with the external view of the body.

9. The computer-assisted medical system of claim 8, wherein the directing of the display device to display the auxiliary shape overlay comprises directing the display device to concurrently display the shape overlay and the auxiliary shape overlay.

10. The computer-assisted medical system of claim 9, wherein the potential field of view indicated by the auxiliary shape overlay corresponds to a previous position at which the active imaging device was located prior to the displaying of the auxiliary shape overlay.

11. The computer-assisted medical system of claim 8, wherein the directing of the display device to display the auxiliary shape overlay comprises directing the display device to abstain from displaying the shape overlay while displaying the auxiliary shape overlay.

12. The computer-assisted medical system of claim 8, wherein:

the active imaging device is configured to provide the captured imagery at different zoom levels, the field of view corresponds to a first zoom level, and the potential field of view corresponds to a second zoom level distinct from the first zoom level; or the active imaging device is configured to capture the imagery of the internal view from different viewing angles, the field of view corresponds to a first viewing angle, and the potential field of view corresponds to a second viewing angle distinct from the first viewing angle; or the active imaging device comprises a pair of stereoscopic image sensors, the field of view corresponds to a first image sensor in the pair of stereoscopic image sensors, and the potential field of view corresponds to a second image sensor in the pair of stereoscopic image sensors; or the active imaging device is configured to capture the imagery of the internal view by way of one imaging technology at a time from a plurality of imaging technologies, the field of view corresponds to a first imaging technology in the plurality of imaging technologies, and the potential field of view corresponds to a second imaging technology in the plurality of imaging technologies.

13. The computer-assisted medical system of claim 1, wherein:

the identifying of the operating condition comprises detecting an initiation, during performance of the operation, of a process to swap out the active imaging device for an additional imaging device;

the directing of the display device to toggle the display of the shape overlay comprises directing the display device to begin displaying the shape overlay at a static position with respect to the body; and the one or more processors are further configured to:
determine, subsequent to the display device beginning to display the shape overlay at the static position, that the display device is to further display an additional shape overlay together with the shape overlay and the external view of the body, the additional shape overlay indicative of an extent, relative to the body, of an additional field of view corresponding to the additional imaging device as the process to swap out the active imaging device for the additional imaging device is performed,
based on the determining that the display device is to display the additional shape overlay, direct the display device to display the additional shape overlay together with the shape overlay and the external view of the body, and
direct the display device to persist in displaying the shape overlay at the static position at least until the additional shape overlay overlaps with the shape overlay at the static position.

14. The computer-assisted medical system of claim 1, wherein:
the identifying of the operating condition comprises detecting an initiation, during performance of the operation, of a process to move the active imaging device from a first port into the body by way of which the active imaging device captures the imagery of the internal view to a second port into the body;
the directing of the display device to toggle the display of the shape overlay comprises directing the display device to begin displaying the shape overlay at a static position with respect to the body; and
the one or more processors are further configured to:
determine, subsequent to the display device beginning to display the shape overlay at the static position, that the display device is to further display an additional shape overlay together with the shape overlay and the external view of the body, the additional shape overlay indicative of an extent, relative to the body, of an additional field of view corresponding to the field of view of the active imaging device as the process to move the active imaging device is performed,
based on the determining that the display device is to display the additional shape overlay, direct the display device to display the additional shape overlay together with the shape overlay and the external view of the body, and
direct the display device to persist in displaying the shape overlay at the static position at least until the additional shape overlay overlaps with the shape overlay at the static position.

15. The computer-assisted medical system of claim 1, wherein:
the identifying of the operating condition comprises detecting an initiation, during performance of the operation, of a process to move the active imaging device from being attached to a first manipulator arm to being attached to a second manipulator arm;
the directing of the display device to toggle the display of the shape overlay comprises directing the display device to begin displaying the shape overlay at a static position with respect to the body; and the one or more processors are further configured to:
determine, subsequent to the display device beginning to display the shape overlay at the static position, that the display device is to further display an additional shape overlay together with the shape overlay and the external view of the body, the additional shape overlay indicative of an extent, relative to the body, of an additional field of view corresponding to the field of view of the active imaging device as the process to move the active imaging device is performed,
based on the determining that the display device is to display the additional shape overlay, direct the display device to display the additional shape overlay together with the shape overlay and the external view of the body, and
direct the display device to persist in displaying the shape overlay at the static position at least until the additional shape overlay overlaps with the shape overlay at the static position.

16. A method comprising:
emitting, by a computer-assisted medical system comprising a manipulator arm coupled to an active imaging device, illumination that illuminates an internal view of a body;
controlling, by the computer-assisted medical system, the active imaging device to capture imagery of an internal view of a body during the illumination;
identifying, by the computer-assisted medical system, an operating condition associated with an operation performed on the body while the active imaging device captures the imagery of the internal view of the body;
determining, by the computer-assisted medical system and based on the identified operating condition, that a display device is to toggle a display of a shape overlay from a first state to a second state while an external view of the body as captured by an external image capture device positioned external to the body is being displayed by the display device, the shape overlay indicative of an extent of a field of view of the active imaging device relative to the body; and
directing, by the computer-assisted medical system and based on the determining that the display device is to toggle the display of the shape overlay from the first state to the second state, the display device to toggle the display of the shape overlay from the first state to the second state, the directing the display device to toggle the display of the shape overlay from the first state to the second state comprising:
directing, when the shape overlay is not being displayed when the operating condition is identified, the display device to begin displaying the shape overlay together with the external view of the body as captured by the external image capture device, and
directing, when the shape overlay is being displayed when the operating condition is identified, the display device to cease displaying the shape overlay together with the external view of the body as captured by the external image capture device.

17. The method of claim 16, wherein the identifying of the operating condition comprises detecting a position of a distal end of the active imaging device in relation to an internal area of the body from which the active imaging device captures the imagery of the internal view.

18. The method of claim 16, wherein the identifying of the operating condition comprises detecting at least one status selected from the group consisting of:

an operational status of an image sensor included in the active imaging device, an operational status of a communication link by way of which the active imaging device provides data associated with the imagery, an operational status of a light source associated with the active imaging device and configured to illuminate an internal area of the body from which the active imaging device captures the imagery, and a status of an object insertion process in which an object is inserted into an internal area of the body.

19. The method of claim 16, wherein:

the identifying of the operating condition comprises detecting that an object is visible within the field of view; and the directing of the display device to toggle the display comprises directing the display device to cease displaying the shape overlay based on the detection that the object is visible within the field of view.

20. The method of claim 16, further comprising:

determining, by the computer-assisted medical system, that the display device is to display an auxiliary shape overlay together with the external view of the body, the auxiliary shape overlay indicative of an extent, relative to the body, of a potential field of view of an auxiliary imaging device or of the active imaging device; and directing, by the computer-assisted medical system and based on the determining that the display device is to display the auxiliary shape overlay, the display device to display the auxiliary shape overlay together with the external view of the body.

21. The method of claim 16, wherein:

the identifying of the operating condition comprises detecting an initiation, during performance of the operation, of a process to swap out the active imaging device for an additional imaging device;

the directing of the display device to toggle the display of the shape overlay comprises directing the display device to begin displaying the shape overlay at a static position with respect to the body; and the method further comprises:

determining, by the computer-assisted medical system subsequent to the display device beginning to display the shape overlay at the static position, that the display device is to further display an additional shape overlay together with the shape overlay and the external view of the body, the additional shape overlay indicative of an extent, relative to the body, of an additional field of view corresponding to the additional imaging device as the process to swap out the active imaging device for the additional imaging device is performed, directing, by the computer-assisted medical system and based on the determining that the display device is to display the additional shape overlay, the display device to display the additional shape overlay together with the shape overlay and the external view of the body, and directing, by the computer-assisted medical system, the display device to persist in displaying the shape overlay at the static position at least until the additional shape overlay overlaps with the shape overlay at the static position.

22. The method of claim 16, wherein:

the identifying of the operating condition comprises detecting an initiation, during performance of the operation, of a process to move the active imaging device from a first port into the body by way of which the active imaging device captures the imagery of the internal view to a second port into the body;

the directing of the display device to toggle the display of the shape overlay comprises directing the display device to begin displaying the shape overlay at a static position with respect to the body; and the method further comprises:

determining, by the computer-assisted medical system subsequent to the display device beginning to display the shape overlay at the static position, that the display device is to further display an additional shape overlay together with the shape overlay and the external view of the body, the additional shape overlay indicative of an extent, relative to the body, of an additional field of view corresponding to the field of view of the active imaging device as the process to move the active imaging device is performed, directing, by the computer-assisted medical system and based on the determining that the display device is to display the additional shape overlay, the display device to display the additional shape overlay together with the shape overlay and the external view of the body, and directing, by the computer-assisted medical system, the display device to persist in displaying the shape overlay at the static position at least until the additional shape overlay overlaps with the shape overlay at the static position.

23. The method of claim 16, wherein:

the identifying of the operating condition comprises detecting an initiation, during performance of the operation, of a process to move the active imaging device from being attached to a first manipulator arm to being attached to a second manipulator arm;

the directing of the display device to toggle the display of the shape overlay comprises directing the display device to begin displaying the shape overlay at a static position with respect to the body; and the method further comprises:

determining, by the computer-assisted medical system subsequent to the display device beginning to display the shape overlay at the static position, that the display device is to further display an additional shape overlay together with the shape overlay and the external view of the body, the additional shape overlay indicative of an extent, relative to the body, of an additional field of view corresponding to the field of view of the active imaging device as the process to move the active imaging device is performed, directing, by the computer-assisted medical system and based on the determining that the display device is to display the additional shape overlay, the display device to display the additional shape overlay together with the shape overlay and the external view of the body, and directing, by the computer-assisted medical system, the display device to persist in displaying the shape overlay at the static position at least until the additional shape overlay overlaps with the shape overlay at the static position.

* * * * *